(12) United States Patent
Forsell

(10) Patent No.: US 7,011,624 B2
(45) Date of Patent: Mar. 14, 2006

(54) MALE IMPOTENCE PROSTHESIS APPARATUS WITH WIRELESS ENERGY SUPPLY

(75) Inventor: Peter Forsell, Zug (CH)

(73) Assignee: Obtech Medical AG, Baar (CH)

( * ) Notice: Subject to any disclaimer, the term of this patent is extended or adjusted under 35 U.S.C. 154(b) by 0 days.

(21) Appl. No.: 10/203,433

(22) PCT Filed: Feb. 14, 2001

(86) PCT No.: PCT/SE01/00310

§ 371 (c)(1),
(2), (4) Date: Nov. 25, 2002

(87) PCT Pub. No.: WO01/47440

PCT Pub. Date: Jul. 5, 2001

(65) Prior Publication Data

US 2003/0135090 A1 Jul. 17, 2003

Related U.S. Application Data

(60) Provisional application No. 60/182,190, filed on Feb. 14, 2000, and provisional application No. 60/182,222, filed on Feb. 14, 2000.

(51) Int. Cl.
*A61F 5/00* (2006.01)

(52) U.S. Cl. .......................................... 600/38; 600/40

(58) Field of Classification Search .............. 600/38–41
See application file for complete search history.

(56) References Cited

U.S. PATENT DOCUMENTS

| 3,954,102 A | 5/1976 | Buuck |
| 4,941,461 A | 7/1990 | Fischell |
| 5,062,416 A | 11/1991 | Stucks |

FOREIGN PATENT DOCUMENTS

EP 0626154 A1 11/1994

*Primary Examiner*—John P. Lacyk
(74) *Attorney, Agent, or Firm*—Nixon & Vanderhye P.C.

(57) ABSTRACT

A male impotence prosthesis apparatus comprises an operable penile prosthesis implanted in an impotent patient's corpus cavernosum to provide flaccid or erect states of the patient's penis. An energy transmission device for wireless transmission of energy from outside the patient's body to inside the patient's body is provided for use in connection with the operation of the penile prosthesis.

335 Claims, 7 Drawing Sheets

MALE IMPOTENCE PROSTHESIS APPARATUS WITH WIRELESS ENERGY SUPPLY

CROSS-REFERENCE TO RELATED APPLICATIONS

This application is the U.S. national phase of international application PCT/SE01/00310, filed in English on 14 Feb. 2001, which designated the U.S. PCT/SE01/00310 claims priority to U.S. provisional application Ser. Nos. 60/182,190, filed 14 Feb. 2000, and 60/182,222, filed 14 Feb. 2000. This application claims the benefit of the filing dates of these two provisional applications.

BACKGROUND OF THE INVENTION

The present invention relates to a male sexual impotence treatment prosthesis apparatus, comprising an operable prosthesis implantable in the cavities of the corpora cavernosa of an impotent patient to provide erect penile condition, when the prosthesis is operated.

Male sexual impotence is a widespread problem. Many different solutions to this problem have been tried. In accordance with a prior system currently practised a hydraulic inflatable/contractible silicon prosthesis is implanted in the cavities of the corpora cavernosa of the penis. In fluid connection with this prosthesis is a reservoir implanted retroperitonially and a pump therefore in the scrotum. By manually pumping the pump the prosthesis is filled with fluid from the reservoir to achieve erect penile condition or is emptied of fluid, which returns to the reservoir, to achieve flaccid penile condition. However, there are several more or less severe disadvantages of this solution. A problem that often occurs is that thick, hard fibrosis is created around the pump, which makes the system useless sooner or later.

Another solution to achieve erection is to restrict the blood flow leaving the penis. For example, U.S. Pat. Nos. 4,829,990, 4,958,630 and 5,048,511 disclose two hydraulically operated inflatable cuffs wrapped around the respective crura or penile exit veins. A disadvantage of such a solution is that it involves complicated surgery. U.S. Pat. No. 4,828,544 discloses another example on this solution, in which an artificial fistula system is surgically implanted and provides a primary fistula between the femoral artery and the femoral vein and a secondary fistula for leading blood from the primary fistula to the penis. An inflatable balloon engages the primary fistula between the secondary fistula and the vein. The balloon is in fluid connection with a manually compressible reservoir implanted in the scrotum. Again, implantation of this artificial fistula system requires delicate surgery.

Yet another solution is to inject a substance in the penile vein system to achieve erection. However, injections are painful and complicated for the patient.

Various impotence treatment devices in which fluid is distributed from a reservoir to an inflatable implanted prosthesis are disclosed in U.S. Pat. Nos. 3,855,122, 3,954,102, 4,009,711, 4,201,202, 4,235,227, 4,318,396 and 5,250,020.

U.S. Pat. No 4,424,807 discloses another solution in which inflatable hydraulic cylindrical elements are implanted relatively deep into the corpus cavernosum.

BRIEF SUMMARY OF THE INVENTION

The object of the present invention is to provide a new convenient male impotence prosthesis apparatus, which does not require manual manipulation of a combined reservoir/pump mechanism as in prior art placed in the scrotum of the patient, when the patient wants to achieve erection.

This object is obtained by an apparatus of the kind stated initially characterised by an energy transmission device for wireless transmission of energy from outside the patient's body to inside the patient's body for use in connection with the operation of the prosthesis, when the prosthesis is implanted.

As a result, the advantage is achieved that the male impotence prosthesis apparatus of the invention provides simple and effective energy transmission, which ensures an extended and reliable functionality of the apparatus, possibly for the rest of the patient's natural life, and at least many years.

Generally, the prosthesis is adapted to control the penis to change, preferably steplessly, between flaccid and erect penile condition. This gives the advantage that the patient is enabled to make fine adjustments of the prosthesis to achieve the desired erection without feeling pain.

Generally, the apparatus comprises an energy transforming device implantable in the patient for transforming the energy wirelessly transmitted by the energy transmission device from a first form into a second form, preferably different than the first form.

The energy transforming device may comprise at least one semiconductor type of component or a circuitry of such semiconductor components. The semiconductor component may comprise a transistor or microchip or similar electronic components. However, the semiconductor component may not comprise rectifying diodes.

In accordance with a main embodiment of the invention, the energy transforming device comprises at least one element having a positive region and a negative region and adapted to create an energy field between the positive and negative regions when exposed to the energy of the first form transmitted by the energy transmission device, so that the energy field provides the energy of the second form. Typically, the above-mentioned semiconductor component may include such an element.

In accordance with a preferred embodiment of the invention, the element comprises an electrical junction element capable of inducing an electric field between the positive and negative regions when exposed to the energy of the first form transmitted by the energy transmission device, whereby the energy of the second form comprises electric energy.

Consequently, the penile prosthesis suitably is electrically operated, whereby the positive and negative regions of the electrical junction element supply electric energy for the operation of the penile prosthesis. The apparatus suitably comprises implantable electric conductors connected to the positive and negative regions of the electrical junction element, whereby the electrical junction element is capable of supplying an electric current, such as a direct current, a pulsating direct current, a combination of a direct and pulsating direct current, an alternating current or a combination of a direct and alternating current, via the conductors. Furthermore, the electrical junction element may be capable of supplying a frequency, amplitude, or frequency and amplitude modulated analog, digital, or a combination of analog and digital signal, which is used in connection with control of the penile prosthesis.

The element, preferably in the form of an electrical semiconductor junction element, should be designed to generate an output current exceeding 1 $\mu$A when exposed to the energy of the first form transmitted by the energy transmission device. Suitably the electrical junction element forms a flat and thin sheet and has a volume of less than 2000 $cm^3$ to be suited for subcutaneous implantation, so that the electrical junction element can be located just behind the skin of the patient. Alternatively, it would be possible to implant the element in the thorax or cephalic region of the patient, or in an orifice of the patient's body and under the mucosa or intraluminar outside the mucosa of the orifice. Of course, all the components of the energy transforming device including the electrical junction element in contact with the patient's body should be of biocompatible material.

For in vitro appliances, a particular type of an electrical semiconductor junction element has been commonly used, namely a so-called p-n (positive/negative) junction element, typically in the form of solar cells. A solar cell transfers solar energy in the form of visible light into electric energy in the form of direct current. For example, a p-n junction element may comprise two layers of semiconductor, one p-type (positive) and the other n-type (negative), sandwiched together to form a "p-n junction". This p-n junction induces an electric field across the element when absorbing quanta of light (photons).

To be more precise, the quanta of light transfer their energy to some of the semiconductor's electrons, which are then able to move about through the material. For each such negatively charged electron, a corresponding positive charge—a "hole"—is created. In an ordinary semiconductor, these electrons and holes recombine after a short time and their energy is wasted as heat. However, when the electrons and holes are swept across the p-n junction in opposite directions by the action of the electric field, the separation of charge induces a voltage across the p-n junction element. By connecting the p-n junction element to an external circuit, the electrons are able to flow thereby creating a current.

Surprisingly, it has been proved that although both the skin and subcutis absorb energy from an external light beam directed against the skin portion behind which a properly designed p-n junction element is located, the light energy transmitted through the skin can induce a current from the p-n junction element strong enough (minimum 1 $\mu A$) to enable the operation of the electrically operated penile prosthesis. Thus, such a p-n junction element is now for the first time used for in vivo applications.

The apparatus may comprise an implantable pulse generator for generating electrical pulses from the energy of the second form produced by the energy field.

Generally, the energy transforming device is adapted to transform the energy of the first form directly or indirectly into the energy of the second form.

In accordance with a preferred embodiment of the invention, the energy of the second form comprises electric energy and the energy transforming device comprises a capacitor, which may be adapted to produce electric pulses from the transformed electric energy. Preferably, the capacitor may be adapted to produce the pulses as the energy transforming device transforms the energy of the first form transmitted by the energy transmission device into the electric energy of the second form. The capacitor should be small to facilitate implantation thereof; i.e. its capacity may not be more than 0.1 $\mu F$.

The apparatus may comprise an implantable stabiliser for stabilising the energy of the second form. Where the energy of the second form comprises electric current the stabiliser may comprise at least one capacitor of the type described above.

In most embodiments of the invention, the apparatus comprises implantable electrical components. Where the electrical components include a capacitor of the type described above or an accumulator, at least one, preferably a single, voltage level guard may advantageously be provided, wherein the charge and discharge of the capacitor or accumulator is controlled by use of the voltage level guard. As a result, there is no need for any implanted current detector and/or charge level detector for the control of the capacitor, which makes the apparatus simple and reliable.

In a particular embodiment of the invention, the wireless energy of the first form comprises sound waves and the energy of the second form comprises electric energy, wherein the energy transforming device is adapted to directly transform the for example sound waves into electric energy.

It should be understood that the energy consuming parts of the apparatus for example a motor or pump may be or may not be energised with the unchanged wirelessly transmitted energy as this being transmitted as well as being or not being energised with energy different than the transmitted energy for example transformed into electrical energy but still directly used for energising the energy consuming parts of the apparatus as the transmitted energy is transmitted. Alternatively the energy consuming parts of the apparatus may be energised from a implanted source of energy or storage device, which still may be loaded with wireless energy. In all these aspects it is preferable to be able to wirelessly control the release of energy and get an feedback of the result of the performed function of the device. Direct use of transmitted energy may be unreliable without a feedback what has happened, has the energy reached it's goal?

The apparatus may comprise an implantable motor or pump for operating the penile prosthesis, wherein the motor or pump is powered by the transformed energy.

In accordance with a main aspect of the invention, the energy transmission device may be adapted to transmit wireless energy for direct use in connection with the operation of the penile prosthesis, as the wireless energy is being transmitted. The advantage of directly using energy as it is transmitted is that the apparatus can be of a very simple design and the few components involved makes the apparatus extremely reliable. For example, the energy transmission device may be adapted to directly power the motor or pump with wireless energy. The wireless energy may comprise a magnetic field or electromagnetic waves, suitably in the form of a signal, for direct power of the motor or pump. All the various functions of the motor and associated components described in the present specification may be used where applicable.

As an alternative to the above-noted main aspect of the invention, the energy transforming device may be adapted to supply the energy of the second form for direct use in connection with the operation of the penile prosthesis, as the energy of the first form is being transformed into the energy of the second form. Consequently, the energy transforming device may be adapted to directly power the motor or pump with the energy of the second form.

Generally, the energy transforming device directly operates the penile prosthesis with the energy of the second form in a non-magnetic, non-thermal or non-mechanical manner.

Where the apparatus comprises a motor, which may be adapted to directly or intermittently operate the penile prosthesis, the energy transforming device may power the motor with the energy of the second form. Suitably, the penile prosthesis is operable to perform a reversible function and the motor is capable of reversing said function.

In accordance with another embodiment of the invention, the penile prosthesis comprises a hydraulic penile prosthesis, and the apparatus comprises an implantable pump for operating the hydraulic penile prosthesis, wherein the energy transforming device supplies the energy of the second form for driving the pump. Preferably, the pump is not a plunger type of pump, but may comprise a peristaltic or membrane pump.

The energy transforming device preferably is capable of generating as the energy of the second form a current exceeding 1 µA, when transferring the energy of the first form transmitted by the energy transmission device.

The apparatus may comprise an implantable adjustment device for adjusting the penile prosthesis to change between erect and flaccid penile states. In accordance with a first alternative the adjustment device is adapted to mechanically adjust the penile prosthesis. In accordance with a second alternative the adjustment device is adapted to hydraulically adjust the penile prosthesis by using implanted hydraulic means. Such hydraulic means may not use hydraulic fluid of the kind having a viscosity that substantially increases when exposed to heat or a magnetic field.

The apparatus of the present invention is not limited to the use of visible light for the wireless transmission of energy. Thus, in accordance with a broad aspect of the invention, the energy transmission device transmits energy by at least one wireless signal, preferably containing radiant energy.

The wireless signal may comprises a wave signal, for example an electromagnetic wave signal, such as an infrared light signal, a visible light signal, an ultra violet light signal, a laser signal, a micro wave signal, a radio wave signal, an x-ray radiation signal, and a gamma radiation signal. Where applicable, one or more of the above signals may be combined. Alternatively, the wave signal may comprise a sound wave signal, such as an ultrasonic signal. Generally, the wireless signal may comprise a digital, analog or a digital and analog signal.

The energy of the first form transmitted by the energy transmission device may comprise an electric or magnetic field transmitted in pulses, for example digital pulses. Furthermore, the energy transforming device may transform the energy of the first form, which may comprise polarised energy, into a direct current, pulsating direct current, a combination of a direct and pulsating direct current, an alternating current or a combination of a direct and alternating current. Alternatively, the energy of the first form may comprise kinetic energy.

The energy of the second form may comprise a frequency, amplitude or frequency and amplitude modulated analog, digital or combined analog and digital signal.

The penile prosthesis may be non-inflatable, i.e. with no hydraulic fluid involved for the adjustments of the penile prosthesis. This eliminates problems with fluid leaking from the penile prosthesis.

The apparatus suitably comprises implantable electric conductors connected to the energy transforming device, whereby the energy transforming device is capable of supplying an electric current, such as direct current, a pulsating direct current, a combination of a direct and pulsating direct current, an alternating current or a combination of a direct and alternating current, via the conductors. Furthermore, the energy transforming device may be capable of supplying a frequency, amplitude, or frequency and amplitude modulated analog, digital, or a combination of analog and digital signal, which is used in connection with control of the penile prosthesis.

In accordance with a main embodiment of the invention, the apparatus comprises an implantable operation device for operating the penile prosthesis and a control device for controlling the operation device, wherein the energy transforming device powers the operation device with the energy of the second form. The operation device preferably comprises a motor, for example an electric linear motor or an electric rotary motor that is controlled by the control device to rotate a desired number of revolutions. Optionally, an implantable gearing may be connected to the motor. The electric motor may have electrically conductive parts made of plastics. Alternatively, the motor may comprise a hydraulic or pneumatic fluid motor, wherein the control device controls the fluid flow through the fluid motor. Motors currently available on the market are getting smaller and smaller. Furthermore, there is a great variety of control methods and miniaturised control equipment available. For example, the number of revolutions of a rotary motor may be analysed by a Hall-element just a few mm in size.

In accordance with another embodiment of the invention, the penile prosthesis comprises hydraulic means and the operation device is adapted to conduct a hydraulic fluid in the hydraulic means. The operation device comprises a fluid conduit connected to the hydraulic means of the penile prosthesis, and a reservoir for fluid, wherein the reservoir forms part of the conduit. The reservoir may form a fluid chamber with a variable volume, and the operation device may be adapted to distribute fluid from the chamber to the hydraulic means of the penile prosthesis by reduction of the volume of the chamber and to withdraw fluid from the hydraulic means to the chamber by expansion of the volume of the chamber. The operation device suitably comprises an implantable motor used for reducing and expanding the volume of the chamber. Also, the operation device may comprise a pump for pumping the hydraulic fluid in the hydraulic means of the penile prosthesis. All of the hydraulic components involved are preferably devoid of any non-return valve. This is of great advantage, because with valves involved there is always a risk of malfunction due to improperly working valves.

The control device may be adapted to reverse the operation device by shifting polarity of the energy of the second form. Where the operation device comprises an electric motor the energy of the second form suitably comprises electric energy.

In accordance with yet another embodiment of the invention, the penile prosthesis is operable to perform a reversible function, such as erecting the penis and then reverse by making the penis flaccid, and there is a reversing device implanted in the patient for reversing the function performed by the penile prosthesis. Such a reversing function preferably involves erecting the penis and making the penis flaccid by the penile prosthesis, suitably in a stepless manner. In this connection, the control device suitably controls the reversing device, which may include a switch, to reverse the function performed by the penile prosthesis. The reversing device may comprise hydraulic means including a valve for shifting the flow direction of a fluid in the hydraulic means. Alternatively, the reversing device may comprise a mechanical reversing device, such as a switch or a gearbox.

Where the reversing device comprises a switch it may be operable by the energy of the second form. In this case, the control device suitably controls the operation of the switch by shifting polarity of the energy of the second form supplied to the switch. The switch may comprise an electric switch and the source of energy may supply electric energy for the operation of the switch.

In accordance with an advantageous embodiment of the invention, the apparatus further comprises an energy storage device implanted in the patient for storing the energy of the second form and for supplying energy in connection with the operation of the penile prosthesis. The implanted energy storage device preferably comprises an electric source of energy, such as an accumulator, a rechargeable battery or a combination of an accumulator and rechargeable battery.

The apparatus may further comprise a switch implantable in the patient for switching the operation of the penile prosthesis and a source of energy implantable in the patient. Such a source of energy preferably is a battery. Alternatively, the source of energy is an accumulator that also may store the energy of the second form.

In accordance with a first alternative, the switch is operated by the energy of the second form supplied by the energy storage device to switch from an off mode, in which the source of energy is not in use, to an on mode, in which the source of energy supplies energy for the operation of the penile prosthesis. In this case, the implanted source of energy may comprise a battery, preferably having a lifetime of at least 10 years, or an accumulator. However, other kinds of sources are also conceivable, such as a nuclear source of energy or a chemical source of energy (fuel cells).

In accordance with a second alternative, the apparatus further comprises a remote control for controlling the supply of energy of the implanted source of energy, wherein the switch is operated by the energy of the second form supplied by the energy storage device to switch from an off mode, in which the remote control is prevented from controlling the source of energy and the source of energy is not in use, to a standby mode, in which the remote control is permitted to control the source of energy to supply energy for the operation of the penile prosthesis.

In accordance with a third alternative, the energy storage device is omitted, wherein the switch is operated by the energy of the second form supplied by the energy transforming device to switch from an off mode, in which the remote control is prevented from controlling the source of energy and the source of energy is not in use, to a standby mode, in which the remote control is permitted to control the source of energy to supply energy for the operation of the penile prosthesis.

In accordance with a fourth alternative, also the remote control is omitted, wherein the switch is operated by the energy of the second form supplied by the energy transforming device to switch from an off mode, in which the source of energy is not in use, to an on mode, in which the source of energy supplies energy for the operation of the penile prosthesis. Where applicable, in the described embodiments the switch may switch when the energy transmission device is transmitting wireless energy, preferably while the transferred energy of the second form is stabilised by an implanted capacitor, which may temporarily (for a few seconds) store the energy of the second form.

In the above noted third and fourth alternatives, the energy transmission device may be substituted for the energy transforming device, whereby the switch is operated by the energy of the first form.

The switch mentioned above may comprise an electronic switch or, where applicable, a mechanical switch.

The advantage of using a switch above all is increased control safety; i.e. interfering signals in the patient's surroundings cannot affect the implanted penile prosthesis. Furthermore, the lifetime of the implanted source of energy will be significantly prolonged, since the energy consumption of the apparatus will be reduced to a minimum. During the above-mentioned standby mode, the remote control uses energy from the implanted source of energy. By means of the energy transmission device energy may be transmitted to activate the switch to connect the implanted source of energy only when energy is required in connection with the operation of the penile prosthesis.

All of the above embodiments may be combined with at least one implantable sensor for sensing at least one physical parameter of the patient, wherein the control device may control the penile prosthesis in response to signals from the sensor. For example, the sensor may sense ejaculation or comprise a pressure sensor for directly or indirectly sensing the pressure in the urethra. The control device may comprise an internal control unit implanted in the patient for, preferably directly, controlling the penile prosthesis in response to signals from the sensor. In response to signals from the sensor, for example ejaculation, pressure, or any other important physical parameter, the internal control unit may send information thereon to outside the patient's body. The control unit may also automatically control the penile prosthesis in response to signals from the sensor. For example, when the penis is in erect state the control unit may control the penile prosthesis to make the penis flaccid in response to the sensor sensing an abnormally high pressure against the penile prosthesis.

Alternatively, the control device may comprise an external control unit outside the patient's body for, suitably directly, controlling the penile prosthesis in response to signals from the sensor. The external control unit may store information on the physical parameter sensed by the sensor and may be manually operated to control the penile prosthesis based on the stored information. In addition, there may be at least one implantable sender for sending information on the physical parameter sensed by the sensor.

An external data communicator may be provided outside the patient's body and an internal data communicator may be implanted in the patient for communicating with the external communicator. The internal communicator may feed data related to the patient, or related to the penile prosthesis, back to the external communicator. Alternatively or in combination, the external communicator may feed data to the internal communicator. The internal communicator may suitably feed data related to at least one physical signal of the patient.

The apparatus may further comprise an implantable programmable control unit for controlling the penile prosthesis, preferably over time in accordance with an activity schedule program. This will advance the apparatus and make possible an adaptation of the apparatus to the individual patients.

Many of the above embodiments are suitably remote controlled. Thus, the apparatus advantageously comprises a wireless remote control transmitting at least one wireless control signal for controlling the penile prosthesis. With such a remote control it will be possible to adapt the function of the apparatus to the patient's need. The control signal may comprise a frequency, amplitude or frequency or amplitude modulated signal. Furthermore, the control signal may comprise an analog or a digital signal, or a combination of an analog and digital signal.

The wireless remote control may be capable of obtaining information on the condition of the implanted penile prosthesis and of controlling the penile prosthesis in response to the information. Also, The remote control may be capable of sending information related to the penile prosthesis from inside the patient's body to the outside thereof.

In a particular embodiment of the invention, the wireless remote control comprises at least one external signal transmitter or transceiver and at least one internal signal receiver or transceiver implantable in the patient. In another particular embodiment of the invention, the wireless remote control comprises at least one external signal receiver or transceiver and at least one internal signal transmitter or transceiver implantable in the patient.

The wireless remote control may transmit a carrier signal for carrying the control signal, wherein the carrier signal is frequency, amplitude or frequency and amplitude modulated. The carrier signal may also comprise digital, analog or a combination of digital and analog signals. Such signals may comprise wave signals. Also the control signal used with the carrier signal may be frequency, amplitude or frequency and amplitude modulated, and be digital, analog or combined digital and analog.

The control signal may comprise a wave signal, for example, a sound wave signal, such as an ultrasound wave signal, an electromagnetic wave signal, such as an infrared light signal, a visible light signal, an ultra violet light signal, a laser signal, a micro wave signal, a radio wave signal, an x-ray radiation signal, or a gamma radiation signal. Where applicable, two or more of the above signals may be combined.

The control signal may be digital or analog, and may comprise an electric or magnetic field. Suitably, the wireless remote control may transmit an electromagnetic carrier wave signal for carrying the digital or analog control signal. For example, use of an analog carrier wave signal carrying a digital control signal would give safe communication. The control signal may be transmitted in pulses by the wireless remote control.

The energy transmission device may function different from or similar to the energy transforming device. For example, the energy transmission and transforming devices function differently when the energy transmission device comprises a coil used for transmitting the energy of the first form and the energy transforming device comprises an electrical junction element for transforming the transmitted energy into the energy of the second form. The energy transmission and transforming devices function similar to each other when the energy transmission device comprises a coil used for transmitting the energy of the first form and the energy transforming device also comprises a coil for transforming the transmitted energy into the energy of the second form.

In accordance with an alternative embodiment of the invention, the apparatus comprises an activatable source of energy implantable in the patient, wherein the source of energy is activated by wireless energy transmitted by the energy transmission device, to supply energy which is used in connection with the operation of the penile prosthesis.

The implantable penile prosthesis suitably is embedded in a soft or gel-like material. For example, a silicone material having hardness less than 20 Shore.

Preferable the present invention provides an a male sexual impotence treatment prosthesis, comprising an prosthesis device implanted in the corpora cavernosa of the patients penis, who suffers from impotence and an adjustment device which temporarely achieve an ereccted status of the penis and an powered operation device which is able to perform a reversible function to adjust said adjustment device.

In another embodiment of the invention the male sexual impotence treatment apparatus, comprising a hydraulic adjustment device, and further comprising a reservoir implantable in the patient and containing hydraulic fluid, and a conduit providing fluid connection between the reservoir and the hydraulic adjustment device, characterised in that the operation device being adapted to operate the hydraulic adjustment device by distributing hydraulic fluid through the conduit between the reservoir and the hydraulic adjustment device, the conduit and hydraulic adjustment device being devoid of any non-return valve to permit free flow of hydraulic fluid in both directions in the conduit.

Another alternative is a pump pumping in only one direction and an adjustable valve to change the direction of fluid to either increase or decrease the amount of fluid in the reservoir. This valve may be manipulated either manually, mechanically, magnetically, or hydraulically.

Alternatively, or in combination with a powered operation device, the servo means may be used, which enables manual manipulation without need for strong manipulation forces. The servo means may comprise hydraulic means, electric control means, magnetic means, or mechanical means, which may be activated by manual manipulating means. Using a servo system will save the use of force when adjusting the adjustment device, which may be of importance in many applications.

The term "servo means" encompasses the normal definition of a servo mechanism, i.e. an automatic device that controls large amounts of power by means of very small amounts of power, but may alternatively or additionally encompass the definition of a mechanism that transfers a weak force acting on a moving element having a long stroke into a strong force acting on another moving element having a short stroke. The servo means may comprise a motor, preferably an electric motor, which may be reversible and/or include a gearing. Where the operation device comprises a motor, the reversing device is adapted to reverse the motor.

The main embodiment of the invention described above including the reservoir may alternatively be equipped with a servo means comprising a reverse servo. The term "reverse servo" is to be understood as a mechanism that transfers a strong force acting on a moving element having a short stroke into a weak force acting on another moving element having a long stroke; i.e. the reverse function of the above-defined alternative mechanism of a normal servo mechanism. A first closed hydraulic system that controls another closed hydraulic system in which hydraulic means of the adjustment device is incorporated may be used. Minor changes in the amount of fluid in a smaller reservoir of the first system could then be transferred by the reverse servo into major changes in the amount of fluid in a larger reservoir in the second system. In consequence, the change of volume in the larger reservoir of the second system affects the hydraulic means of the adjustment device. For example, a short stroke that decreases the volume of the smaller reservoir will cause the larger reservoir to supply the adjustment device with a large amount of hydraulic fluid, which in turn results in a long mechanical adjustment stroke on the restriction device.

The great advantage of using such a reverse servo is that the larger volume system could be placed inside the abdomen or retroperitoneum where there is more space and still it would be possible to use manual manipulation means of the smaller system subcutaneously. The smaller reservoir could be controlled directly or indirectly by a fluid supply means. The fluid supply means may include another small reservoir, which may be placed subcutaneously and may be activated by manual manipulation means. Both the normal servo means and the specific reverse servo may be used in connection with all of the various components and solutions described in the present specification.

Thus, the reverse servo may be adapted to provide relative displacement between the first and second wall portions of the reservoir, suitably in response to the pressure in the reservoir, in order to change the volume of the chamber of the reservoir.

Generally, the servo means, including the reverse servo, comprises a pressure controlled servo means. The alarm mentioned above may alternatively be adapted to generate an alarm signal in response to the lapse of a predetermined time period during which the pressure controlling the servo means exceeds a predetermined high value.

The reverse servo may comprise magnetic means, electric means or manual manipulation means or a combination thereof. Preferably, however, the reverse servo comprises hydraulic means.

In accordance with a particular embodiment of the invention, the reverse servo further comprises a servo reservoir defining a chamber containing servo fluid, and the operation device comprise first and second wall portions of the servo reservoir, which are displaceable relative to each other to change the volume of the chamber of the servo reservoir. The first and second wall portions of the servo reservoir may be displaceable relative to each other by magnetic means, hydraulic means, or electric control means.

Where the reverse servo comprises hydraulic means it may further comprise a fluid supply reservoir connected to the servo reservoir in a closed system and containing a further predetermined amount of fluid. The fluid supply reservoir defines a chamber for the further predetermined amount of fluid and the operation device is adapted to change the volume of the chamber and thereby control the amount of fluid in the servo reservoir. The fluid supply reservoir comprises first and second wall portions, which are displaceable relative to each other to change the volume of the chamber of the fluid supply reservoir. Suitable, the fluid supply reservoir increases the amount of fluid in the servo reservoir in response to a predetermined first displacement of the first wall portion of the fluid supply reservoir relative to the second wall portion of the fluid supply reservoir and decreases the amount of fluid in the servo reservoir in response to a predetermined second displacement of the first wall portion of the fluid supply reservoir relative to the second wall portion of the fluid supply reservoir.

All the above described various components, such as the motor, pump and capacitor, may be combined in the different embodiments where applicable. Also the various functions described in connection with the above embodiments of the invention may be used in different applications, where applicable.

All the various ways of transferring, transforming and controlling energy presented in the present specification may be practised by using all of the various components and solutions described.

The present invention also provides a method for implanting the male impotence prosthesis apparatus described above comprising the steps of cutting an opening in an impotent patient's mucosa in an orifice of the patient's body, and implanting the energy transforming device of the apparatus in the patient's body through the opening. Alternatively, the cutting step may comprise cutting an opening in the patient's skin and the implanting step may comprise implanting the energy transforming device in the patient's body through the opening.

There is also provided a laparascopical implanting method, in accordance with a first alternative, comprising the steps of providing the male impotence prosthesis apparatus described above, placing at least two laparascopic cannula within an impotent patient's body, and implanting the energy transforming device of the apparatus in the patient's body by using the at least two laparascopic cannula.

BRIEF DESCRIPTION OF THE DRAWINGS

The invention is described in more detail in the following with reference to the accompanying drawings, in which.

DETAILED DESCRIPTION OF THE INVENTION

Figure 1:
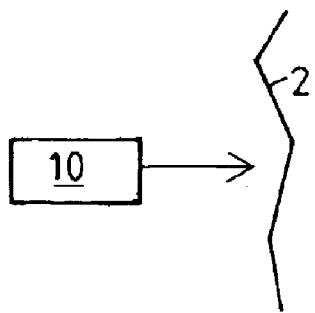
FIGS. 1 to 12 are schematic block diagrams illustrating twelve embodiments, respectively, of the male impotence prosthesis apparatus of the invention, in which wireless energy is transmitted from outside a patient's body to energy consuming components of the apparatus implanted in the patient.
Figure 1:
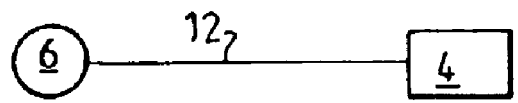

Referring to the drawing figures, like reference numerals designate identical or corresponding elements throughout the several figures.

FIG. 1 schematically shows a most simple embodiment of the male impotence prosthesis apparatus of the invention having some parts implanted in a patient and other parts located outside the patient's body. Thus, in FIG. 1 all parts placed to the right of the patient's skin 2 are implanted and all parts placed to the left of the skin 2 are located outside the patient's body.

The apparatus of FIG. 1 comprises an operable penile prosthesis 4 placed in the cavities of the corpora cavernosa of an impotent patient's penis. The implanted prosthesis 4 is capable of performing a reversible function, i.e. to erect the penis or to make the penis flaccid. An implanted energy transforming device 6 is adapted to supply energy consuming components of the penile prosthesis 4 with energy via a power supply line 12. An external energy transmission device 10 includes a wireless remote control transmitting a wireless signal, which is received by a signal receiver incorporated in the implanted energy transforming device 6. The implanted energy transforming device 6 transforms energy from the signal into electric energy which is supplied via the power supply line 12.

Figure 2:
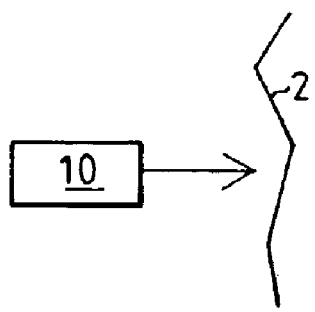
Figure 2:
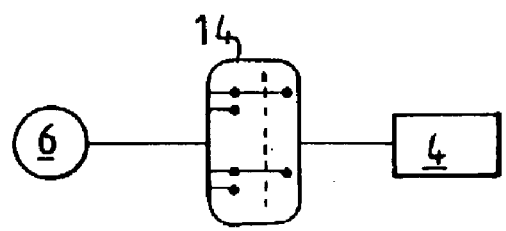

FIG. 2 shows an embodiment of the invention identical to that of FIG. 1, except that a reversing device in the form of an electric switch 14 operable by polarised energy also is implanted in the patient for reversing the penile prosthesis 4. The wireless remote control of the external energy transmission device 10 transmits a wireless signal that carries polarised energy and the implanted energy transforming device 6 transforms the wireless polarized energy into a polarized current for operating the switch 14. When the polarity of the current is shifted by the energy transforming device 6 the switch 14 reverses the function performed by the penile prosthesis 4.

Figure 3:
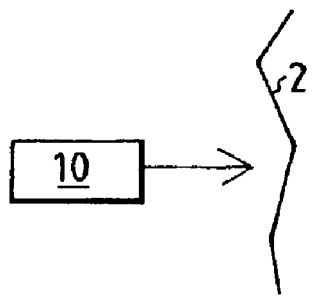
Figure 3:
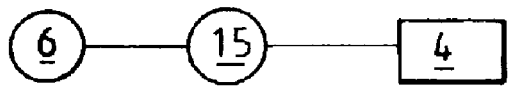

FIG. 3 shows an embodiment of the invention identical to that of FIG. 1, except that an operation device in the form of a motor 15 for operating the penile prosthesis 4 also is implanted in the patient. The motor 15 is powered with energy from the energy transforming device 6, as the remote control of the external energy transmission device 10 transmits a wireless signal to the receiver of the energy transforming device 6.

Figure 4:
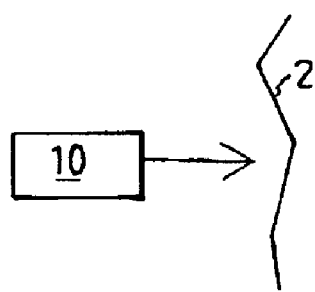
Figure 4:
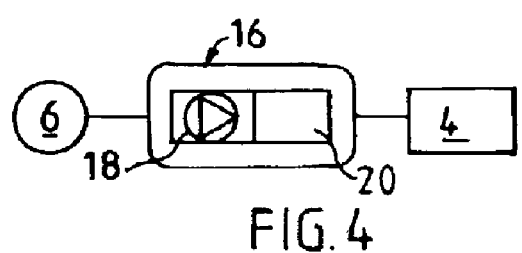

FIG. 4 shows an embodiment of the invention identical to that of FIG. 1, except that an assembly 16 including a motor/pump unit 18 and a fluid reservoir 20 also is implanted in the patient. In this case the penile prosthesis 4 is hydraulically operated, i.e. hydraulic fluid is pumped by the motor/pump unit 18 from the reservoir 20 through a conduit 22 to the penile prosthesis 4 to erect the patients penis, and hydraulic fluid is pumped by the motor/pump unit 18 back from the penile prosthesis 4 to the reservoir 20 to make the penis flaccid. The implanted energy transforming device unit 6 transforms wireless energy into a current, for example a polarized current, for powering the motor/pump unit 18 via an electric power supply line 24.

Figure 5:
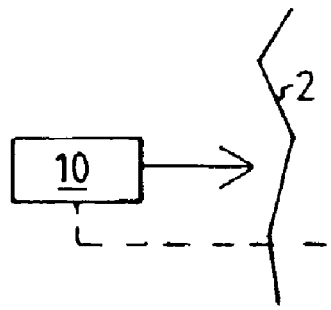
Figure 5:
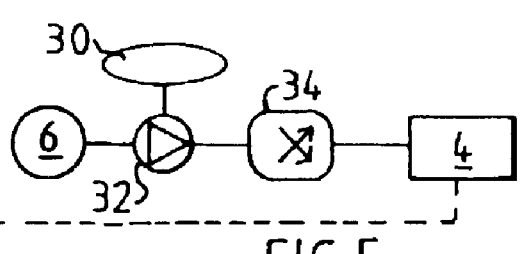

FIG. 5 shows an embodiment of the invention comprising the external energy transmission device 10 with its wireless remote control, the penile prosthesis 4, in this case hydraulically operated, and the implanted energy transforming device 6, and further comprising an implanted hydraulic fluid reservoir 30, an implanted motor/pump unit 32 and an implanted reversing device in the form of a hydraulic valve shifting device 34. The motor of the motor/pump unit 32 is an electric motor. In response to a control signal from the wireless remote control of the external energy transmission device 10, the implanted energy transforming device 6 powers the motor/pump unit 32 with energy from the energy carried by the control signal, whereby the motor/pump unit 32 distributes hydraulic fluid between the reservoir 30 and the penile prosthesis 4. The remote control of the energy transmission device 10 controls the shifting device 34 to shift the hydraulic fluid flow direction between one direction in which the fluid is pumped by the motor/pump unit 32 from the reservoir 30 to the penile prosthesis 4 to erect the penis, and another opposite direction in which the fluid is pumped by the motor/pump unit 32 back from the penile prosthesis 4 to the reservoir 30 to make the penis flaccid.

Figure 6:
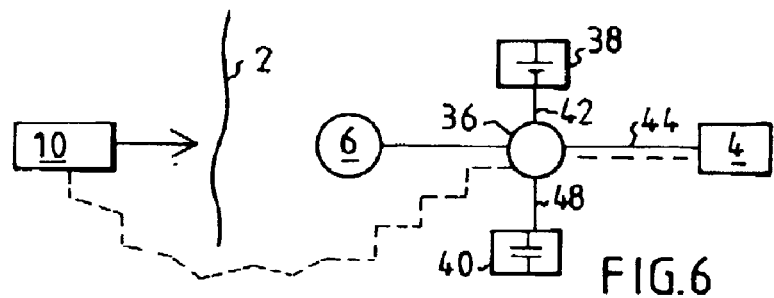

FIG. 6 shows an embodiment of the invention identical to that of FIG. 1, except that a control unit 36 controlled by the wireless remote control of the external energy transmission device 10, an accumulator 38 and a capacitor 40 also are implanted in the patient. The control unit 36 stores electric energy received from the energy transforming device 6 in the accumulator 38, which supplies energy to the penile prosthesis 4. In response to a control signal from the wireless remote control of the energy transmission device 10, the control unit 6 either releases electric energy from the accumulator 38 and transforms the released energy via power lines 42 and 44, or directly transforms electric energy from the energy transforming device 6 via a power line 46, the capacitor 40, which stabilizes the electric current, a power line 48 and the power line 44, for the operation of the penile prosthesis 4.

In accordance with an alternative, the capacitor 40 in the embodiment of FIG. 6 may be omitted. In accordance with another alternative, the accumulator 38 in this embodiment may be omitted.

Figure 7:
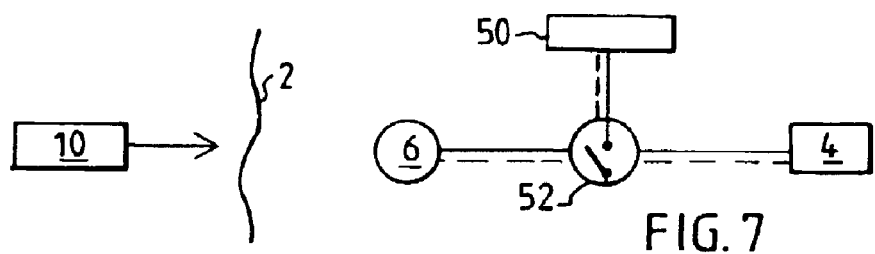

FIG. 7 shows an embodiment of the invention identical to that of FIG. 1, except that a battery 50 for supplying energy for the operation of the penile prosthesis 4 and an electric switch 52 for switching the operation of the penile prosthesis 4 also are implanted in the patient. The switch 52 is operated by the energy supplied by the energy transforming device 6 to switch from an off mode, in which the battery 50 is not in use, to an on mode, in which the battery 50 supplies energy for the operation of the penile prosthesis 4.

Figure 8:
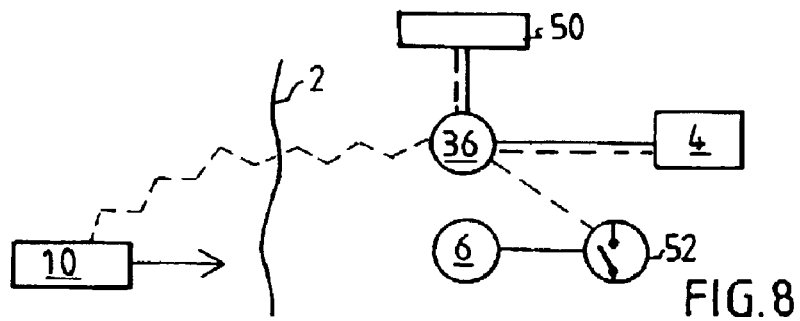

FIG. 8 shows an embodiment of the invention identical to that of FIG. 7, except that a control unit 36 controllable by the wireless remote control of the external energy transmission device 10 also is implanted in the patient. In this case, the switch 52 is operated by the energy supplied by the energy transforming device 6 to switch from an off mode, in which the wireless remote control is prevented from controlling the control unit 36 and the battery is not in use, to a standby mode, in which the remote control is permitted to control the control unit 36 to release electric energy from the battery 50 for the operation of the penile prosthesis 4.

Figure 9:
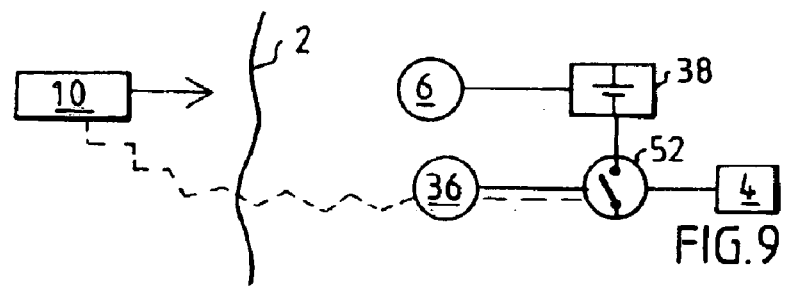

FIG. 9 shows an embodiment of the invention identical to that of FIG. 8, except that an accumulator 38 is substituted for the battery 50 and the implanted components are interconnected differently. In this case, the accumulator 38 stores energy from the energy transforming device 6. In response to a control signal from the wireless remote control of the external energy transmission device 10, the implanted control unit 36 controls the switch 52 to switch from an off mode, in which the accumulator 38 is not in use, to an on mode, in which the accumulator 38 supplies energy for the operation of the penile prosthesis 4.

Figure 10:
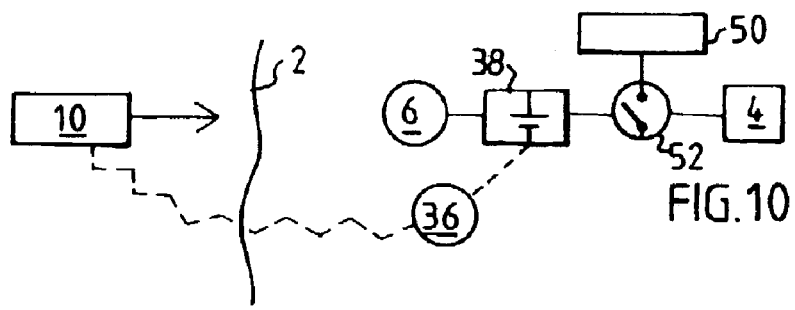

FIG. 10 shows an embodiment of the invention identical to that of FIG. 9, except that a battery 50 also is implanted in the patient and the implanted components are interconnected differently. In response to a control signal from the wireless remote control of the external energy transmission device 10, the implanted control unit 36 controls the accumulator 38 to deliver energy for operating the switch 52 to switch from an off mode, in which the battery 50 is not in use, to an on mode, in which the battery 50 supplies electric energy for the operation of the penile prosthesis 4.

Alternatively, the switch 52 may be operated by energy supplied by the accumulator 38 to switch from an off mode, in which the wireless remote control is prevented from controlling the battery 50 to supply electric energy and is not in use, to a standby mode, in which the wireless remote control is permitted to control the battery 50 to supply electric energy for the operation of the penile prosthesis 4.

Figure 11:
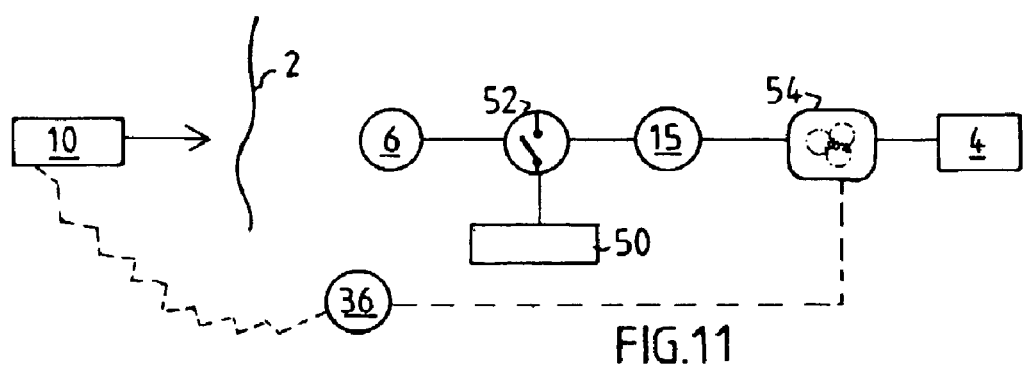

FIG. 11 shows an embodiment of the invention identical to that of FIG. 7, except that a motor 15, a mechanical reversing device in the form of a gear box 54 and a control unit 36 for controlling the gear box 54 also are implanted in the patient. The implanted control unit 36 controls the gear box 54 to reverse the function performed by the penile prosthesis 4 (mechanically operated).

Figure 12:
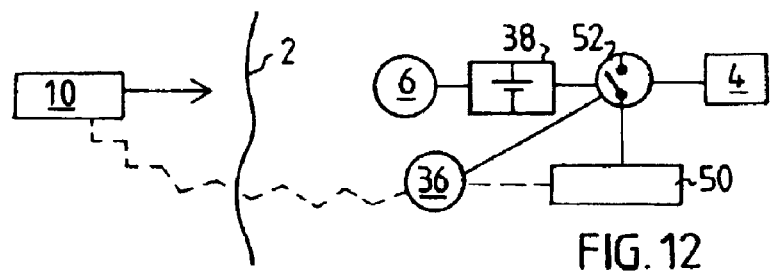

FIG. 12 shows an embodiment of the invention identical to that of FIG. 10 except that the implanted components are interconnected differently. Thus, in this case the control unit 36 is powered by the battery 50 when the accumulator 38, suitably a capacitor, activates the switch 52 to switch to an on mode. When the switch 52 is in its on mode the control unit 36 is permitted to control the battery 50 to supply, or not supply, energy for the operation of the penile prosthesis 4.

Figure 13:
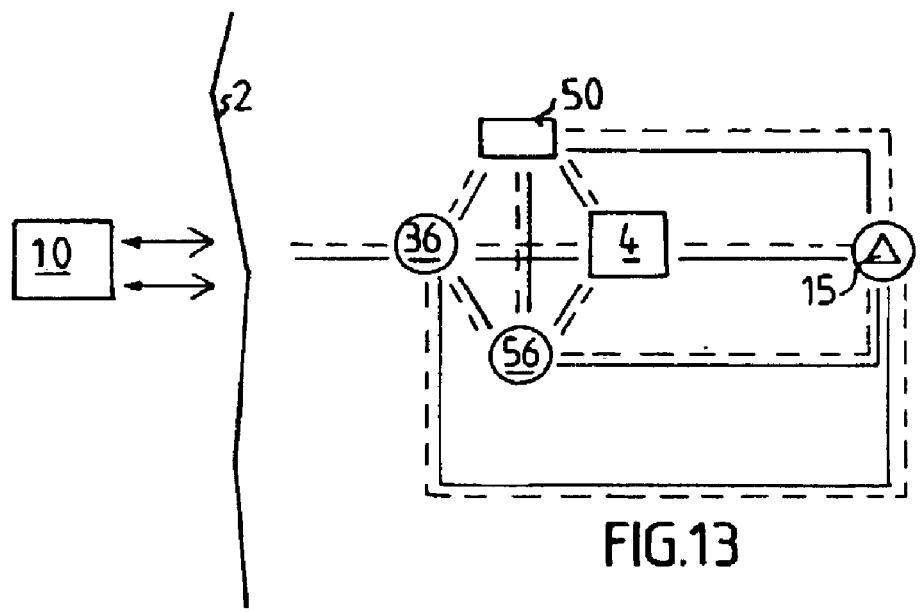
FIG. 13 is a schematic block diagram illustrating conceivable combinations of implanted components for achieving various communication options.

FIG. 13 schematically shows conceivable combinations of implanted components of the apparatus for achieving various communication options. Basically, there are the implanted penile prosthesis 4, control unit 36 and motor/pump unit 18, and the external energy transmission device 10 including the external wireless remote control. As already described above the wireless remote control transmits a control signal which is received by the implanted control unit 36, which in turn controls the various implanted components of the apparatus.

A sensor 56 may be implanted in the patient for sensing a physical parameter of the patient, such as the pressure in the erected penis tissue. The implanted control unit 36, or alternatively the external wireless remote control of the energy transmission device 10, may control the penile prosthesis 4 in response to signalss from the sensor 56. A tranceiver may be combined with the sensor 56 for sending information on the sensed physical parameter to the external wireless remote control. The wireless remote control may comprise a signal transmitter or tranceiver and the implanted control unit 36 may comprise a signal receiver or transciever. Alternatively, the wireless remote control may comprise a signal reciever or transceiver and the implanted control unit 36 may comprise a signal transmitter or transceiver. The above tranceivers, transmitters and receivers may be used for sending information or data related to the penile prosthesis 4 from inside the patient's body to the outside thereof.

Where the motor/pump unit 18 and battery 50 for powering the motor/pump unit 18 are implanted, the battery 50 may be equipped with a tranceiver for sending information on the condition of the battery 50.

Those skilled in the art will realize that the above various embodiments according to FIGS. 1–13 could be combined in many different ways. For example, the polarized energy operated switch 14 could be incorporated in any of the embodiments of FIGS. 3, 6–12, the hydraulic shifting device 34 could be incorporated in the embodiment of FIG. 4, and the gear box 54 could be incorporated in the embodiment of FIG. 3.

Figure 14:
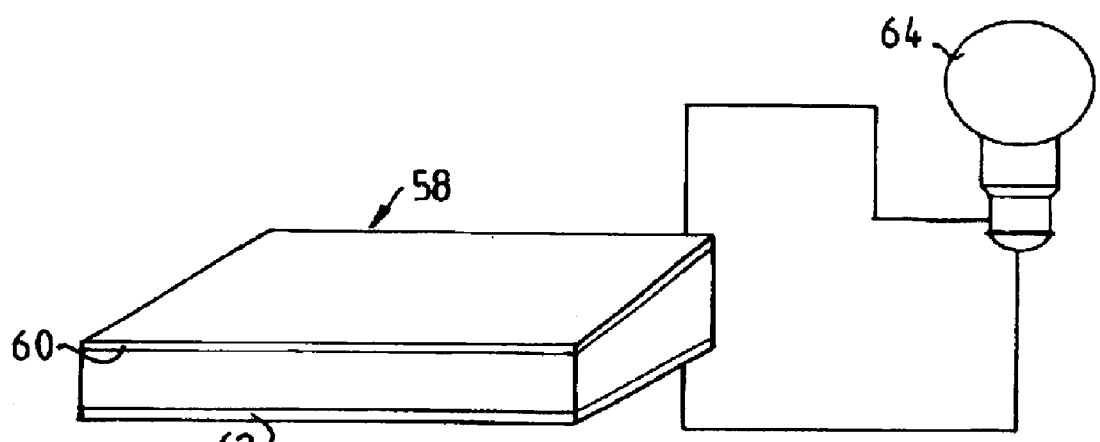
FIG. 14 illustrates an electrical junction element for use in the apparatus of the present invention.

FIG. 14 shows an energy transforming device in the form of an electrical junction element 58 for use in any of the above embodiments according to FIGS. 1–13. The element 58 is a flat p-n junction element comprising a p-type semiconductor layer 60 and an n-type semiconductor layer 62 sandwiched together. A light bulb 64 is electrically connected to opposite sides of the element 58 to illustrate how the generated current is obtained. The output of current from such a p-n junction element 58 is correlated to the temperature. See the formula below.

$$I=I0(\exp(qV/kT)-1)$$

where

I is the external current flow,

I0 is the reverse saturation current, q is the fundamental electronic charge of 1.602×10–19 coulombs, V is the applied voltage, k is the Boltzmann constant, and T is the absolute temperature.

Under large negative applied voltage (reverse bias), the exponential term becomes negligible compared to 1.0, and I is approximately –I0. I0 is strongly dependent on the temperature of the junction and hence on the intrinsic-carrier concentration. I0 is larger for materials with smaller bandgaps than for those with larger bandgaps. The rectifier action of the diode—that is, its restriction of current flow to only one direction—is in this particular embodiment the key to the operation of the p-n junction element 58.

An alternative way to design a p-n junction element is to deposit a thin layer of semiconductor onto a supporting material which does not absorb the kind of energy utilized in the respective embodiments. For use with wirelessly transmitted energy in terms of light waves, glass could be a suitable material. Various materials may be used in the semiconductor layers such as but not limited to cadmium telluride, copper-indium-diselenide and silicon. It is also possible to use a multilayer structure with several layers of p and n-type materials to improve efficiency.

The electric energy generated by the p-n junction element 58 could be of the same type as generated by solar cells, in which the negative and positive fields create a direct current. Alternatively, the negative and positive semiconductor layers may change polarity following the transmitted waves, thereby generating an alternating current.

The p-n junction element 58 is designed to make it suited for implantation. Thus, all the external surfaces of the element 58 in contact with the human body are made of a biocompatible material. The p-n junction semiconductors are designed to operate optimally at a body temperature of 37 C because the current output, which should be more than 1 A, is significantly depending on temperature as shown above. Since both the skin and subcutis absorb energy, the relation between the sensitivity or working area of the element 58 and the intensity or strength of the wireless energy transmission is considered. The p-n junction element 58 preferably is designed flat and small. Alternatively, if the element 58 is made in larger sizes it should be flexible, in order to adapt to the patient's body movements. The volume of the element 58 should be kept less than 2000 cm$^3$.

Figure 15:
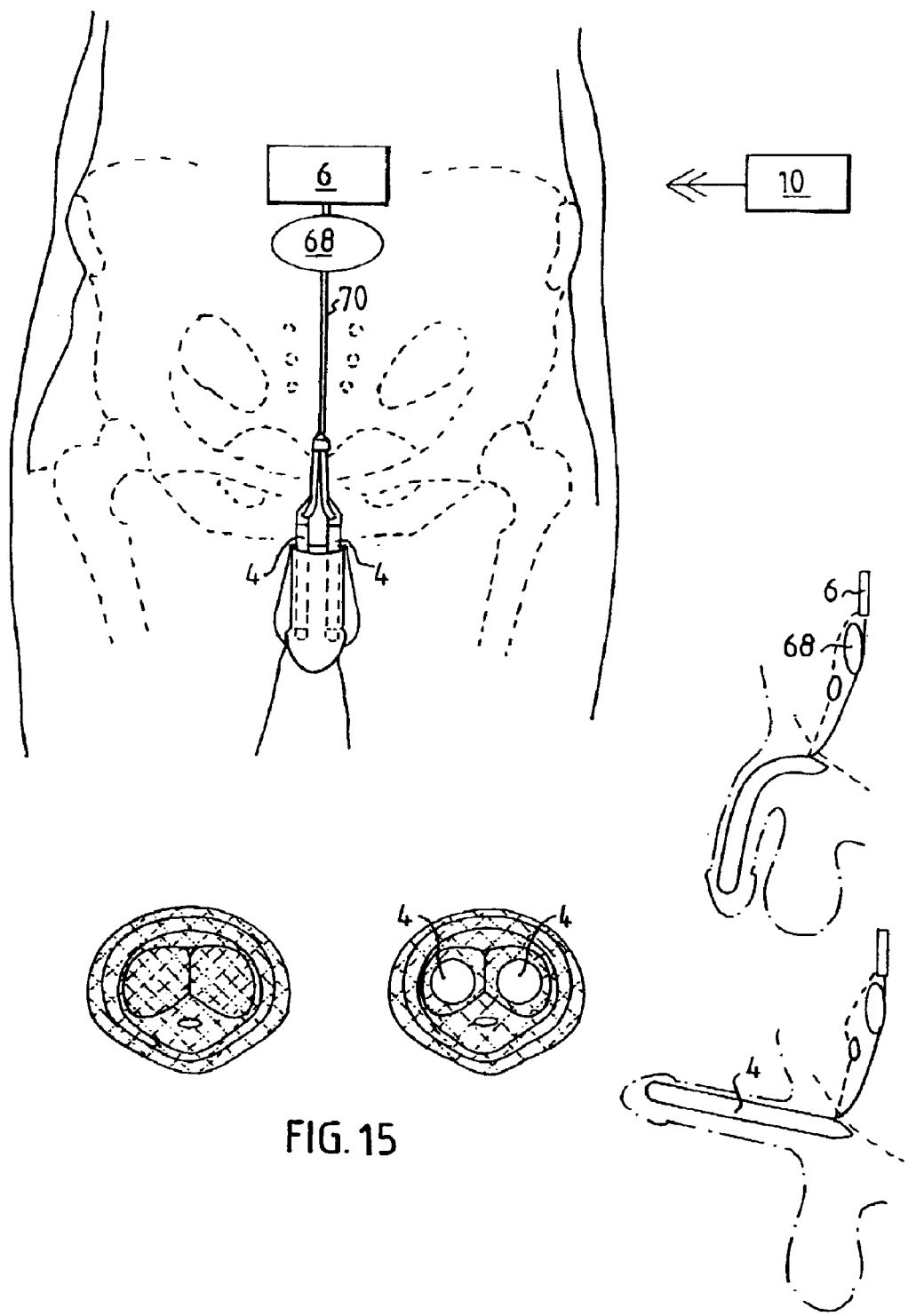
FIG. 15 illustrates the apparatus in accordance with the invention implanted in a patient.

FIG. 15 generally illustrates how any of the above-described embodiments of the male impotence prosthesis apparatus of the invention may be implanted in a patient. Thus, a penile prosthesis 4 implanted in a patient engages the penile tissue and the prolongation thereof to provide flaccid or erected conditions of the patient's penis. An implanted operation device 68, such as an electric motor or a motor/pump assembly, operates the penile prosthesis 4 through a transmission member 70, such as a mechanical transmission cord or a fluid tube. An energy transforming device in the form of an element 6 having a positive region and a negative region, as described above in more detail, is placed underneath the skin of the patient.

Wireless energy carried by a signal transmitted by a wireless remote control of an external energy transmission device 10 at least partly penetrates the patient's skin and hits the element 6. The energy thus hitting the element 6 is transformed into energy of a different form that is suited for powering the operation device 68. For example, where the operation device 68 is an electric motor the element 6 comprises an electric p-n junction element that transforms the wireless energy into an electric current for powering the electric motor. Where the operation device 68 comprises a pump, the element 6 may transform the wireless energy into kinetic energy for powering the pump.

The transformed energy may be utilized for directly operating the penile prosthesis 4 or, where the penile prosthesis 4 is electrically operated, for storage in a capacitor and/or an accumulator for later or parallel use. Preferably (but not necessarily) the element 6 is controlled by a microprocessor. The wireless remote control of the external energy transmission device 10 is used to control the utilization of the transmitted energy and any function or command to/from the implanted penile prosthesis 4.

Figure 16:
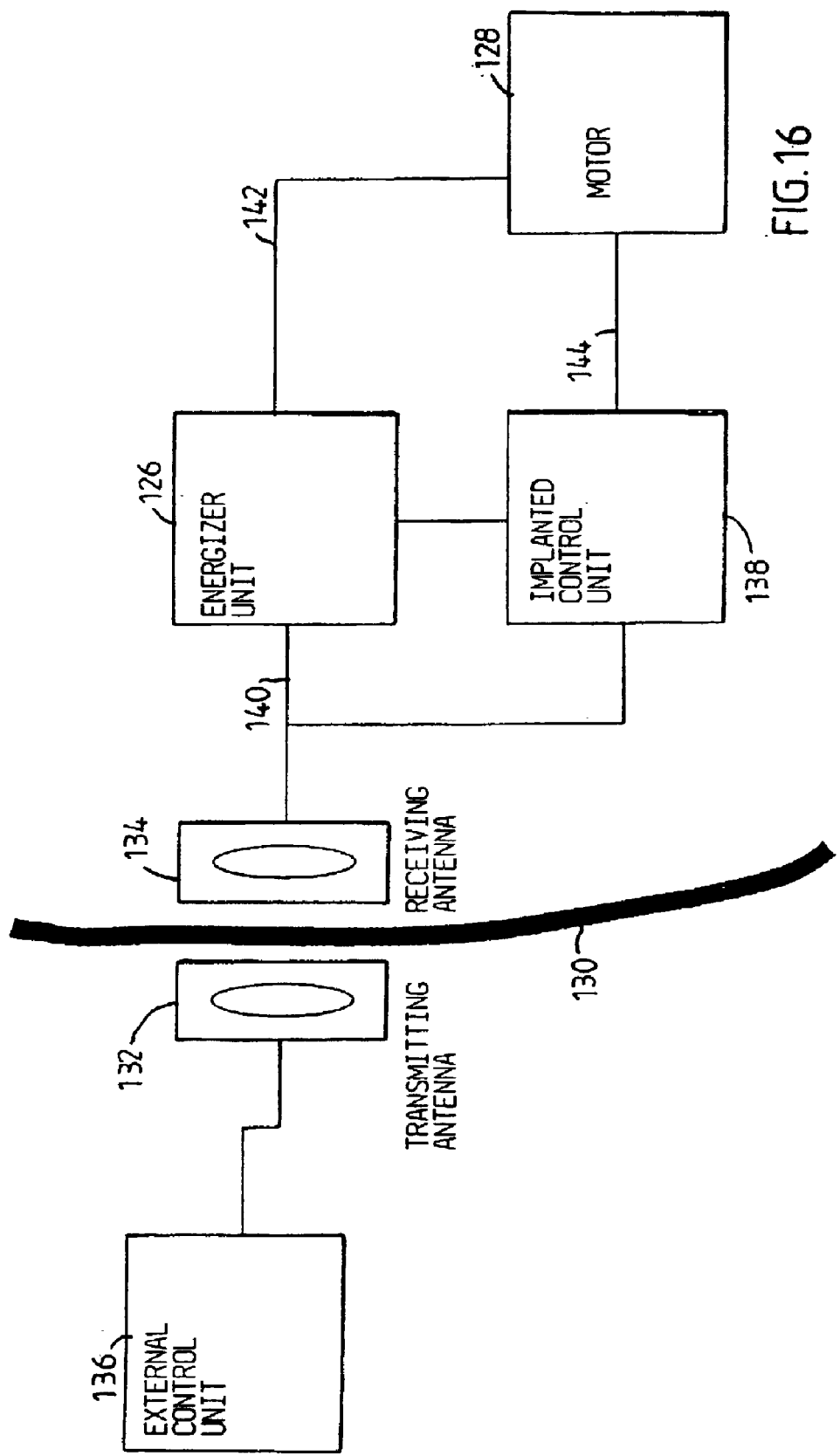
FIG. 16 is a block diagram illustrating remote control components of an embodiment of the invention, in which wireless energy is transmitted by the use of electromagnetic signals.

FIG. 16 shows the basic parts of a wireless remote control of the apparatus of the invention including an electric motor 128 for operating a restriction member, for example of the type illustrated in FIG. 15. In this case, the remote control is based on the transmission of electromagnetic wave signals, often of high frequencies in the order of 100 kHz–1 gHz, through the skin 130 of the patient. In FIG. 15, all parts placed to the left of the skin 130 are located outside the patient's body and all parts placed to the right of the skin 130 are implanted. Any suitable remote control system may be used.

An external signal transmitting antenna 132 is to be positioned close to a signal receiving antenna 134 implanted close to the skin 130. As an alternative, the receiving antenna 134 may be placed for example inside the abdomen of the patient. The receiving antenna 134 comprises a coil, approximately 1–100 mm, preferably 25 mm in diameter, wound with a very thin wire and tuned with a capacitor to a specific high frequency. A small coil is chosen if it is to be implanted under the skin, or in the scrotum and pelvic region of the patient and a large coil is chosen if it is to be implanted in the abdomen of the patient. The transmitting antenna 132 comprises a coil having about the same size as the coil of the receiving antenna 134 but wound with a thick wire that can handle the larger currents that is necessary. The coil of the transmitting antenna 132 is tuned to the same specific high frequency as the coil of the receiving antenna 134.

An external control unit 136 comprises a microprocessor, a high frequency electromagnetic wave signal generator and a power amplifier. The microprocessor of the control unit 136 is adapted to switch the generator on/off and to modulate signals generated by the generator to send digital information via the power amplifier and the antennas 132, 134 to an implanted control unit 138. To avoid that accidental random high frequency fields trigger control commands, digital signal codes are used. A conventional keypad placed on the external control unit 136 is connected to the microprocessor thereof. The keypad is used to order the microprocessor to send digital signals to either contract or enlarge the penile prosthesis. The microprocessor starts a command by applying a high frequency signal on the antenna 132. After a short time, when the signal has energized the implanted parts of the control system, commands are sent to contract or enlarge the penile prosthesis in predefined steps. The commands are sent as digital packets in the form illustrated below.

| Start pattern, | Command, | Count, | Checksum, |
|---|---|---|---|
| 8 bits | 8 bits | 8 bits | 8 bits |

The commands are sent continuously during a rather long time period (e.g. about 30 seconds or more). When a new contract or enlarge step is desired the Count byte is increased by one to allow the implanted control unit 138 to decode and understand that another step is demanded by the external control unit 136. If any part of the digital packet is erroneous, its content is simply ignored.

Through a line 140, an implanted energizer unit 126 draws energy from the high frequency electromagnetic wave signals received by the receiving antenna 134. The energizer unit 126 stores the energy in an energy storage device, such as a large capacitor, powers the control unit 138 and powers the electric motor 128 via a line 142.

The control unit 138 comprises a demodulator and a microprocessor. The demodulator demodulates digital signals sent from the external control unit 136. The microprocessor of the control unit 138 receives the digital packet, decodes it and, provided that the power supply of the energizer unit 126 has sufficient energy stored, sends a signal via a signal line 144 to the motor 128 to either contract or enlarge the penile prosthesis depending on the received command code.

Alternatively, the energy stored in the energy storage device of the energizer unit may only be used for powering a switch, and the energy for powering the motor 128 may be obtained from another implanted energy source of relatively high capacity, for example a battery. In this case the switch is adapted to connect said battery to the control unit 138 in an on mode when said switch is powered by the energy storage device and to keep the battery disconnected from the control unit in a standby mode when the switch is unpowered.

Figure 17:
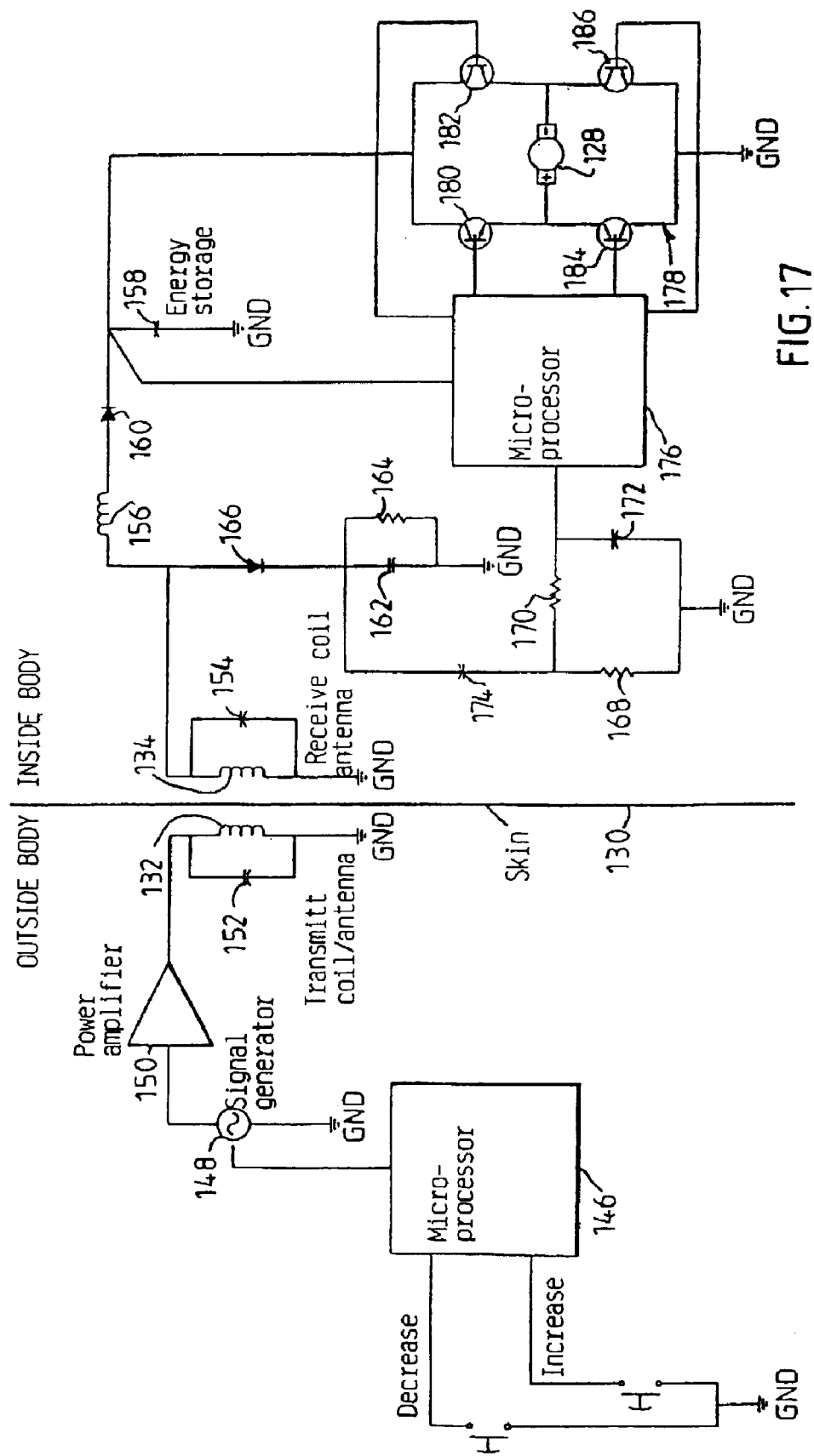
FIG. 17 is a schematic view of exemplary circuitry used for the components of the block diagram of FIG. 16.

With reference to FIG. 17, the remote control schematically described above will now be described in accordance with a more detailed embodiment. The external control unit 136 comprises a microprocessor 146, a signal generator 148 and a power amplifier 150 connected thereto. The microprocessor 146 is adapted to switch the signal generator 148 on/off and to modulate signals generated by the signal generator 148 with digital commands that are sent to implanted components of the apparatus. The power amplifier 150 amplifies the signals and sends them to the external signal transmitting antenna 132. The antenna 132 is connected in parallel with a capacitor 152 to form a resonant circuit tuned to the frequency generated by the signal generator 148.

The implanted signal receiving antenna coil 134 forms together with a capacitor 154 a resonant circuit that is tuned to the same frequency as the transmitting antenna 132. The signal receiving antenna coil 134 induces a current from the received high frequency electromagnetic waves and a rectifying diode 160 rectifies the induced current, which charges a storage capacitor 158. A coil 156 connected between the antenna coil 134 and the diode 160 prevents the capacitor 158 and the diode 160 from loading the circuit of the signal receiving antenna 134 at higher frequencies. Thus, the coil 156 makes it possible to charge the capacitor 158 and to transmit digital information using amplitude modulation.

A capacitor 162 and a resistor 164 connected in parallel and a diode 166 forms a detector used to detect amplitude modulated digital information. A filter circuit is formed by a resistor 168 connected in series with a resistor 170 connected in series with a capacitor 172 connected in series with the resistor 168 via ground, and a capacitor 174, one terminal of which is connected between the resistors 168, 170 and the other terminal of which is connected between the diode 166 and the circuit formed by the capacitor 162 and resistor 164. The filter circuit is used to filter out undesired low and high frequencies. The detected and filtered signals are fed to an implanted microprocessor 176 that decodes the digital information and controls the motor 128 via an H-bridge 178 comprising transistors 180,182,184 and 186. The motor 128 can be driven in two opposite directions by the H-bridge 178.

The microprocessor 176 also monitors the amount of stored energy in the storage capacitor 158. Before sending signals to activate the motor 128, the microprocessor 176 checks whether the energy stored in the storage capacitor 158 is enough. If the stored energy is not enough to perform the requested operation, the microprocessor 176 waits for the received signals to charge the storage capacitor 158 before activating the motor 128.

The invention also comprises or consists of the foregoing structures and method steps, and is to be interpreted as broadly as allowed by the prior art.

What is claimed is:

1. A male sexual impotence treatment prosthesis apparatus, comprising:
   an operable prosthesis implantable in the cavities of the corpora cavernosa of an impotent patient to provide erect penile condition, when the prosthesis is operated,
   an energy transmission device for wireless transmission of energy of a first form from outside the patient's body to inside the patient's body for use in connection with the operation of the prosthesis, when the prosthesis is implanted, and
   an energy transforming device implantable in the patient for transforming the energy of the first form wirelessly transmitted by the energy transmission device into energy of a second form, the penile prosthesis being operable in response to the energy of the second form,
   wherein the energy transforming device includes at least one element having a positive region and a negative region, the element creates an energy field between the positive and negative regions when exposed to the energy of the first form transmitted by the energy transmission device, and the energy field produces the energy of the second form.

2. An apparatus according to claim 1, wherein the energy of the second form is different than the energy of the first form.

3. An apparatus according to claim 1, wherein the element comprises an electrical junction element, and the electrical junction element induces an electric field between the positive and negative regions when exposed to the energy of the first form transmitted by the energy transmission device, whereby the energy of the second form comprises electric energy.

4. An apparatus according to claim 3, wherein the penile prosthesis is electrically operated, and the positive and negative regions of the electrical junction element supply electric energy for the operation of the penile prosthesis.

5. An apparatus according to claim 4, further comprising electric conductors connected to the positive and negative regions of the electrical junction element, whereby the electrical junction element supplies an electric current via the conductors.

6. An apparatus according to claim 5, wherein the electrical junction element supplies a direct current or pulsating direct current via the conductors.

7. An apparatus according to claim 5, wherein the electrical junction element supplies an alternating current or a combination of a direct and alternating current via the conductors.

8. An apparatus according to claim 4, wherein the electrical junction element supplies a frequency or amplitude modulated signal.

9. An apparatus according to claim 4, wherein the electrical junction element supplies an analog or digital signal.

10. An apparatus according to claim 1, wherein the energy transforming device forms a flat and thin sheet, and has a volume of less than 2000 cm$^3$.

11. An apparatus according to claim 1, wherein the energy transforming device is adapted to transform the energy of the first form directly or indirectly into the energy of the second form.

12. An apparatus according to claim 11, further comprising an implantable motor or pump for operating the penile prosthesis, wherein the motor or pump is powered by the energy of the second form.

13. An apparatus according to claim 12, wherein the energy transforming device is adapted to directly power the motor or pump by the transformed energy, as the energy of the second form is being transformed from the energy of the first form.

14. An apparatus according to claim 11, wherein the energy of the first form comprises sound waves and the energy of the second form comprises electric energy.

15. An apparatus according to claim 1, wherein the energy transforming device comprises a capacitor and the energy of the second form comprises electric energy.

16. An apparatus according to claim 15, wherein the capacitor is adapted to produce electric pulses from the transformed electric energy.

17. An apparatus according to claim 16, wherein the capacitor is adapted to produce the pulses of the electric energy, as the energy transforming device transforms the energy of the first form transmitted by the energy transmission device into the electric energy of the second form.

18. An apparatus according to claim 1, further comprising an implantable stabiliser for stabilising the energy of the second form.

19. An apparatus according to claim 18, wherein the energy of the second form comprises electric current and the stabiliser comprises at least one capacitor.

20. An apparatus according to claim 1, further comprising implantable electrical components including at least one voltage level guard.

21. An apparatus according to claim 1, further comprising implantable electrical components including a single voltage level guard.

22. An apparatus according to claim 20, wherein the electrical components are devoid of any current detector and/or charge level detector.

23. An apparatus according to claim 20, further comprising an implantable capacitor or accumulator, wherein the charge or discharge of the capacitor or accumulator is controlled by use of the voltage level guard.

24. An apparatus according to claim 15, wherein the capacitor has a capacity less than 0.1 $\mu$F.

25. An apparatus according to claim 1, wherein the energy transmission device is adapted to transmit wireless energy for direct use in connection with the operation of the penile prosthesis, as the wireless energy is being transmitted.

26. An apparatus according to claim 1, wherein the energy transforming device is adapted to supply the energy of the second form for direct use in connection with the operation of the penile prosthesis, as the energy of the first form is being transformed into the energy of the second form.

27. An apparatus according to claim 26, further comprising an implantable motor or pump for operating the penile prosthesis, wherein the energy transforming device is adapted to directly power the motor or pump with the energy of the second form.

28. An apparatus according to claim 27, wherein the energy transforming device directly operates the penile prosthesis with the energy of the second form in a non-magnetic, non-thermal or non-mechanical manner.

29. An apparatus according to claim 1, further comprising an implantable motor for direct or intermittent operation of the penile prosthesis, wherein the energy transforming device powers the motor with the energy of the second form.

30. An apparatus according to claim 29, wherein the penile prosthesis is operable to perform a reversible function and the motor is adapted to reverse said function.

31. An apparatus according to claim 1, wherein the penile prosthesis comprises a hydraulic penile prosthesis, and further comprising an implantable pump for operating the hydraulic penile prosthesis, the energy transforming device supplying the energy of the second form for driving the pump.

32. An apparatus according to claim 31, wherein the pump is not a plunger type of pump.

33. An apparatus according to claim 1, wherein the energy transforming device generates as the energy of the second form a current exceeding 1 µA, when transferring the energy of the first form transmitted by the energy transmission device.

34. An apparatus according to claim 1, further comprising an adjustment device for adjusting the penile prosthesis to change between erect and flaccid penile states, wherein the adjustment device is adapted to mechanically adjust the penile prosthesis, or adapted to hydraulically adjust the penile prosthesis by using hydraulic means which is devoid of hydraulic fluid of the kind having a viscosity that substantially increases when exposed to heat or a magnetic field.

35. An apparatus according to claim 1, wherein the energy transforming device comprises at least one semiconductor type of component.

36. An apparatus according to claim 35, wherein the energy transforming device comprises a circuitry of semiconductor components.

37. An apparatus according to claim 35, wherein the semiconductor component comprises a transistor or microchip or similar electronic components excluding rectifying diodes.

38. An apparatus according to claim 36, wherein the semiconductor component comprises said element having a positive region and a negative region.

39. An apparatus according to claim 1, further comprising an implantable operation device for operating the penile prosthesis, wherein the energy transforming device powers the operation device with the energy of the second form.

40. An apparatus according to claim 39, further comprising a control device for controlling the operation device.

41. An apparatus according to claim 39, wherein the operation device comprises a motor.

42. An apparatus according to claim 41, further comprising an implantable gearing connected to the motor.

43. An apparatus according to claim 41, wherein the motor comprises a rotary motor and the control device controls the rotary motor to rotate a desired number of revolutions.

44. An apparatus according to claim 41, wherein the motor comprises a linear motor.

45. An apparatus according to claim 41, wherein the motor comprises a hydraulic or pneumatic fluid motor, and the control device controls the fluid motor.

46. An apparatus according to claim 41, wherein the motor comprises an electric motor having electrically conductive parts made of plastics.

47. An apparatus according to claim 39, wherein the penile prosthesis comprises hydraulic means and the operation device is adapted to conduct a hydraulic fluid in the hydraulic means.

48. An apparatus according to claim 47, wherein the operation device comprises a fluid conduit connected to the hydraulic means of the penile prosthesis, and a reservoir for fluid, the reservoir forming part of the conduit.

49. An apparatus according to claim 48, wherein the hydraulic means and conduit are devoid of any non-return valve.

50. An apparatus according to claim 49, wherein the reservoir forms a fluid chamber with a variable volume, and the operation device is adapted to distribute fluid from the chamber to the hydraulic means of the penile prosthesis by reduction of the volume of the chamber and to withdraw fluid from the hydraulic means to the chamber by expansion of the volume of the chamber.

51. An apparatus according to claim 50, wherein the operation device comprises an implantable motor used for reducing and expanding the volume of the chamber.

52. An apparatus according to claim 47, wherein the operation device comprises an implantable pump for pumping the hydraulic fluid in the hydraulic means of the penile prosthesis.

53. An apparatus according to claim 40, wherein the control device shifts polarity of the energy of the second form to reverse the operation device.

54. An apparatus according to claim 41, wherein the operation device comprises an electric motor and the energy of the second form comprises electric energy.

55. An apparatus according to claim 1, wherein the penile prosthesis is operable to perform a reversible function.

56. An apparatus according to claim 55, further comprising a reversing device implantable in the patient for reversing the function performed by the penile prosthesis.

57. An apparatus according to claim 56, further comprising a control device, wherein the control device controls the reversing device to reverse the function performed by the penile prosthesis.

58. An apparatus according to claim 56, wherein the reversing device comprises hydraulic means including a valve for shifting the flow direction of a fluid flow in the hydraulic means.

59. An apparatus according to claim 56, wherein the reversing device comprises a mechanical reversing device.

60. An apparatus according to claim 59, wherein the reversing device comprises a gearbox.

61. An apparatus according to claim 56, wherein the reversing device comprises a switch.

62. An apparatus according to claim 61, wherein the switch is operable by the energy of the second form.

63. An apparatus according to claim 62, further comprising a control device, wherein the control device controls the operation of the switch by shifting polarity of the energy of the second form.

64. An apparatus according to claim 62, wherein the switch comprises an electric switch and the energy of the second form comprises electric energy.

65. An apparatus according to claim 39, wherein the operation device comprises hydraulic means and at least one valve for controlling a fluid flow in the hydraulic means.

66. An apparatus according to claim 65, further comprising a wireless remote control for controlling the valve.

67. An apparatus according to claim 1, further comprising a control device adapted to control the energy transforming device to produce the energy of the second form in a train of energy pulses for direct use in connection with the operation of the penile prosthesis.

68. An apparatus according to claim 1, further comprising an energy storage device implantable in the patient for storing the energy of the second form and for supplying energy in connection with the operation of the penile prosthesis.

69. An apparatus according to claim 68, wherein the energy storage device comprises an accumulator.

70. An apparatus according to claim 69, wherein the energy of the second form comprises electric energy and the energy storage device comprises an electric accumulator.

71. An apparatus according to claim 70, wherein the electric accumulator comprises at least one capacitor or at least one rechargeable battery, or a combination of at least one capacitor and at least one rechargeable battery.

72. An apparatus according to claim 1, further comprising a switch implantable in the patient for directly or indirectly switching the operation of the penile prosthesis.

73. An apparatus according to claim 72, further comprising an energy storage device implantable in the patient for storing the energy of the second form and a source of energy implantable in the patient, wherein the switch is operated by the energy of the second form supplied by the energy storage device to switch from an off mode, in which the source of energy is not in use, to an on mode, in which the source of energy supplies energy for the operation of the penile prosthesis.

74. An apparatus according to claim 72, further comprising an energy storage device implantable in the patient for storing the energy of the second form and a source of energy implantable in the patient, and a remote control for controlling the supply of energy of the source of energy, wherein the switch is operated by the energy of the second form supplied by the energy storage device to switch from an off mode, in which the remote control is prevented from controlling the source of energy and the source of energy is not in use, to a standby mode, in which the remote control is permitted to control the source of energy to supply energy for the operation of the penile prosthesis.

75. An apparatus according to claim 72, further comprising a source of energy implantable in the patient for supplying energy for the operation of the penile prosthesis, wherein the switch is operated by the energy of the second form supplied by the energy transforming device to switch from an off mode, in which the source of energy is not in use, to an on mode, in which the source of energy supplies energy for the operation of the penile prosthesis.

76. An apparatus according to claim 72, further comprising a source of energy implantable in the patient for supplying energy for the operation of the penile prosthesis, and a remote control for controlling the supply of energy of the implantable source of energy, wherein the switch is operated by the energy of the second form supplied by the energy transforming device to switch from an off mode, in which the remote control is prevented from controlling the source of energy and the source of energy is not in use, to a standby mode, in which the remote control is permitted to control the source of energy to supply energy for the operation of the penile prosthesis.

77. An apparatus according to claim 72, further comprising a source of energy implantable in the patient for supplying energy for the operation of the penile prosthesis, wherein the switch is operated by the energy of the first form supplied by the energy transmission device to switch from an off mode, in which the source of energy is not in use, to an on mode, in which the source of energy supplies energy for the operation of the penile prosthesis.

78. An apparatus according to claim 72, further comprising a source of energy implantable in the patient for supplying energy for the operation of the penile prosthesis, and a remote control for controlling the supply of energy of the implantable source of energy, wherein the switch is operated by the energy of the first form supplied by the energy transmission device to switch from an off mode, in which the remote control is prevented from controlling the source of energy and the source of energy is not in use, to a standby mode, in which the remote control is permitted to control the source of energy to supply energy for the operation of the penile prosthesis.

79. An apparatus according to claim 1, wherein the penile prosthesis is electrically operated, and the energy of the second form comprises electric energy.

80. An apparatus according to claim 79, further comprising electric conductors connected to the energy transforming device, whereby the energy transforming device supplies an electric current via the conductors.

81. An apparatus according to claim 1, wherein the energy transforming device supplies a frequency, amplitude or frequency and amplitude modulated signal.

82. An apparatus according to claim 1, wherein the energy transforming device supplies an analog, digital or a combination of an analog and digital signal.

83. An apparatus according to claim 1, further comprising an activatable source of energy implantable in the patient, wherein the source of energy is activated by wireless energy transmitted by the energy transmission device, to supply energy which is used in connection with the operation of the penile prosthesis.

84. An apparatus according to claim 1, wherein the energy transmission device transmits energy by at least one wireless signal.

85. An apparatus according to claim 84, wherein the signal contains radiant energy.

86. An apparatus according to claim 84, wherein the signal comprises a wave signal.

87. An apparatus according to claim 86, wherein the wave signal comprises an electromagnetic wave signal including one of an infrared light signal, a visible light signal, an ultra violet light signal, a laser signal, a micro wave signal, a radio wave signal, an x-ray radiation signal, and a gamma radiation signal.

88. An apparatus according to claim 86, wherein the wave signal comprises a sound or ultrasound wave signal.

89. An apparatus according to claim 84, wherein the signal comprises a digital or analog signal, or a combination of a digital and analog signal.

90. An apparatus according to claim 1, wherein the energy of the first form transmitted by the energy transmission device comprises an electric, an electromagnetic or a magnetic field, or a combination thereof.

91. An apparatus according to claim 90, wherein the electric, electromagnetic or magnetic field, or the combination thereof is transmitted in pulses or digital pulses, or a combination of pulses and digital pulses by the energy transmission device.

92. An apparatus according to claim 90, wherein the electric, electromagnetic or magnetic field, or the combination thereof is transmitted in waves or analog pulses or a combination thereof by the energy transmission device.

93. An apparatus according to claim 1, wherein the energy transforming device transforms the energy of the first form into a direct current or pulsating direct current, or a combination of a direct current and pulsating direct current.

94. An apparatus according to claim 1, wherein the energy transforming device transforms the energy of the first form into an alternating current or a combination of a direct and alternating current.

95. An apparatus according to claim 1, further comprising an implantable pulse generator for generating electrical pulses from the energy of the second form produced by the energy field.

96. An apparatus according to claim 1, further comprising at least one implantable sensor for sensing at least one physical parameter of the patient, preferably ejaculation.

97. An apparatus according to claim 96, wherein the sensor comprises a pressure sensor for directly or indirectly sensing as the physical parameter the pressure in the urethra.

98. An apparatus according to claim 96, further comprising a control device for controlling the penile prosthesis in response to signals from the sensor.

99. An apparatus according to claim 98, wherein the control device comprises an internal control unit implantable in the patient for controlling the penile prosthesis in response to signals from the sensor.

100. An apparatus according to claim 99, wherein the internal control unit directly controls the penile prosthesis in response to signals from the sensor.

101. An apparatus according to claim 98, wherein the control device comprises an external control unit outside the patient's body for controlling the penile prosthesis in response to signals from the sensor.

102. An apparatus according to 101, wherein the external control unit stores information on the physical parameter sensed by the sensor and is manually operated to control the penile prosthesis based on the stored information.

103. An apparatus according to claim 96, further comprising at least one implantable sender for sending information on the physical parameter sensed by the sensor.

104. An apparatus according to claim 1, further comprising a wireless remote control for transmitting at least one wireless control signal for controlling the penile prosthesis.

105. An apparatus according to 104, wherein the control signal comprises a frequency, amplitude or frequency or amplitude modulated signal.

106. An apparatus according to 104, wherein the control signal comprises an analog or a digital signal, or a combination of an analog and digital signal.

107. An apparatus according to claim 104, wherein the remote control is adapted to obtain information on the condition of the implantable penile prosthesis and to control the penile prosthesis in response to the information.

108. An apparatus according to claim 104, wherein the remote control comprises an implantable control unit for controlling the penile prosthesis.

109. An apparatus according to claim 108, wherein the control unit comprises a microprocessor.

110. An apparatus according to claim 104, wherein the wireless remote control comprises at least one external signal transmitter or transceiver and at least one internal signal receiver or transceiver implantable in the patient.

111. An apparatus according to claim 104, wherein the wireless remote control comprises at least one external signal receiver or transceiver and at least one internal signal transmitter or transceiver implantable in the patient.

112. An apparatus according to claim 104, wherein the remote control is adapted to send information related to the penile prosthesis from inside the patients body to the outside thereof.

113. An apparatus according to claim 112, wherein the remote control controls the penile prosthesis in response to the information.

114. An apparatus according to claim 104, wherein the remote control comprises a control signal transmitter for transmitting the wireless control signal, and the energy transmission device comprises the control signal transmitter, whereby energy is transmitted by the control signal.

115. An apparatus according to claim 104, wherein the energy transmission device transmits energy by at least one signal separate from the control signal.

116. An apparatus according to claim 104, wherein the remote control transmits a carrier signal for carrying the control signal.

117. An apparatus according to claim 104, wherein the energy transmission device transmits energy by at least one signal, which is used as a carrier signal for the control signal transmitted by the remote control.

118. An apparatus according to claim 117, wherein the carrier signal is frequency, amplitude or frequency and amplitude modulated.

119. An apparatus according to claim 117, wherein the carrier signal comprises digital, analog or a combination of digital and analog signals.

120. An apparatus according to claim 119, wherein the signals comprise wave signals.

121. An apparatus according to claim 104, wherein the control signal comprises a wave signal comprising one of a sound wave signal, an ultrasound wave signal, an electromagnetic wave signal, an infrared light signal, a visible light signal, an ultra violet light signal, a laser light signal, a micro wave signal, a radio wave signal, an x-ray radiation signal and a gamma radiation signal.

122. An apparatus according to claim 104, wherein the control signal comprises an electric or magnetic field, or a combined electric and magnetic field.

123. An apparatus according to claim 106, wherein the remote control transmits an electromagnetic carrier wave signal for carrying the digital or analog control signal.

124. An apparatus according to claim 1, wherein the energy of the second form used for operating the penile prosthesis is wirelessly transmitted by the energy transforming device.

125. An apparatus according to claim 1, further comprising an implantable control unit for controlling the penile prosthesis.

126. An apparatus according to claim 125, wherein the control unit is programmable for controlling the penile prosthesis in accordance with a program.

127. An apparatus according to claim 125, wherein the control unit controls the penile prosthesis over time in accordance with an activity schedule program.

128. An apparatus according to claim 125, further comprising an external wireless remote control for programming the implantable control unit.

129. An apparatus according to claim 1, further comprising an external data communicator and an implantable internal data communicator communicating with the external data communicator, wherein the internal communicator feeds data related to the penile prosthesis back to the external data communicator or the external data communicator feeds data to the internal data communicator.

130. An apparatus according to claim 129, wherein the internal data communicator feeds data related to at least one physical signal of the patient.

131. An apparatus according to claim 1, wherein the penile prosthesis is adapted to control the erect and flaccid states of the patient's penis.

132. An apparatus according to claim 1, wherein the penile prosthesis is non-inflatable.

133. An apparatus according to claim 1, wherein the energy of the first form comprises magnetic energy, kinetic energy, sound energy, chemical energy, radiant energy, electromagnetic energy, or nuclear energy.

134. An apparatus according to claim 1, wherein one of the energy of the first form and the energy of the second form is non-magnetic, non-kinetic, non-chemical, non-sonic, non-nuclear or non-thermal.

135. An apparatus according to claim 1, wherein the energy transmission device functions different from the energy transforming device.

136. An apparatus according to claim 1, wherein the energy of the first form comprises photo energy or thermal energy.

137. An apparatus according to claim 1, wherein the penile prosthesis is embedded in a soft or gel-like material.

138. An apparatus according to claim 1, wherein the penile prosthesis is embedded in a silicone material having hardness less than 20 Shore.

139. A male sexual impotence treatment prosthesis apparatus, comprising:

an operable prosthesis implantable in the cavities of the corpora cavernosa of an impotent patient to provide erect penile condition, when the prosthesis is operated, an energy transmission device for wireless transmission of energy of a first form from outside the patient's body to inside the patient's body for use in connection with the operation of the prosthesis, when the prosthesis is implanted, an energy transforming device implantable in the patient for transforming the energy of the first form wirelessly transmitted by the energy transmission device into energy of a second form, the penile prosthesis being operable in response to the energy of the second form, an energy storage device implantable in the patient for storing the energy of the second form and for supplying energy in connection with the operation of the penile prosthesis, and a control device for transmitting a control signal from outside the patients body to control the supply of energy from the energy storage device.

140. An apparatus according to claim 139, wherein the energy storage device comprises an accumulator.

141. An apparatus according to claim 140, wherein the energy of the second form comprises electric energy and the energy storage device comprises an electric accumulator.

142. An apparatus according to claim 141, wherein the electric accumulator comprises at least one capacitor or at least one rechargeable battery, or a combination of at least one capacitor and at least one rechargeable battery.

143. An apparatus according to claim 139, further comprising a switch implantable in the patient for directly or indirectly switching the operation of the penile prosthesis.

144. An apparatus according to claim 143, further comprising a source of energy implantable in the patient, wherein the switch is operated by the energy of the second form supplied by the energy storage device to switch from an off mode, in which the source of energy is not in use, to an on mode, in which the source of energy supplies energy for the operation of the penile prosthesis.

145. An apparatus according to claim 143, further comprising a source of energy implantable in the patient, wherein the control device comprises a wireless remote control for controlling the supply of energy of the source of energy and the switch is operated by the energy of the second form supplied by the energy storage device to switch from an off mode, in which the remote control is prevented from controlling the source of energy and the source of energy is not in use, to a standby mode, in which the remote control is permitted to control the source of energy to supply energy for the operation of the penile prosthesis.

146. An apparatus according to claim 139, wherein the energy of the second form is different than the energy of the first form.

147. An apparatus according to claim 139, wherein the energy transforming device comprises at least one element having a positive region and a negative region, the element is capable of creating an energy field between the positive and negative regions when exposed to the energy of the first form transmitted by the energy transmission device, and the energy field produces the energy of the second form.

148. An apparatus according to claim 147, wherein the element comprises an electrical junction element, and the electrical junction element induces an electric field between the positive and negative regions when exposed to the energy of the first form transmitted by the energy transmission device, whereby the energy of the second form comprises electric energy.

149. An apparatus according to claim 148, wherein the penile prosthesis is electrically operated, and the positive and negative regions of the electrical junction element supply electric energy for the operation of the penile prosthesis.

150. An apparatus according to claim 149, further comprising electric conductors connected to the positive and negative regions of the electrical junction element, whereby the electrical junction element supplies an electric current via the conductors.

151. An apparatus according to claim 150, wherein the electrical junction element supplies a direct current or pulsating direct current via the conductors.

152. An apparatus according to claim 150, wherein the electrical junction element supplies an alternating current or a combination of a direct and alternating current via the conductors.

153. An apparatus according to claim 149, wherein the electrical junction element supplies a frequency or amplitude modulated signal.

154. An apparatus according to claim 149, wherein the electrical junction element supplies an analog or digital signal.

155. An apparatus according to claim 139, wherein the energy transforming device forms a flat and thin sheet, and has a volume of less than 2000 $cm^3$.

156. An apparatus according to claim 139, wherein the energy transforming device is adapted to transform the energy of the first form directly or indirectly into the energy of the second form.

157. An apparatus according to claim 156, further comprising an implantable motor or pump for operating the penile prosthesis, wherein the motor or pump is powered by the energy of the second form.

158. An apparatus according to claim 156, wherein the energy of the first form comprises sound waves and the energy of the second form comprises electric energy.

159. An apparatus according to claim 139, wherein the energy transforming device comprises a capacitor and the energy of the second form comprises electric energy.

160. An apparatus according to claim 159, wherein the capacitor is adapted to produce electric pulses from the transformed electric energy.

161. An apparatus according to claim 160, wherein the capacitor is adapted to produce the pulses of the electric energy, as the energy transforming device transforms the energy of the first form transmitted by the energy transmission device into the electric energy of the second form.

162. An apparatus according to claim 139, further comprising an implantable stabiliser for stabilising the energy of the second form.

163. An apparatus according to claim 162, wherein the energy of the second form comprises electric current and the stabiliser comprises at least one capacitor.

164. An apparatus according to claim 139, further comprising implantable electrical components including at least one voltage level guard.

165. An apparatus according to claim 139, further comprising implantable electrical components including a single voltage level guard.

166. An apparatus according to claim 164, wherein the electrical components are devoid of any current detector and/or charge level detector.

167. An apparatus according to claim 164, further comprising an implantable capacitor or accumulator, wherein the charge or discharge of the capacitor or accumulator is controlled by use of the voltage level guard.

168. An apparatus according to claim 159, wherein the capacitor has a capacity less than 0.1 $\mu$F.

169. An apparatus according to claim 139, further comprising an implantable motor for direct or intermittent operation of the penile prosthesis, wherein the energy storage device powers the motor.

170. An apparatus according to claim 169, wherein the penile prosthesis is operable to perform a reversible function and the motor is adapted to reverse said function.

171. An apparatus according to claim 139, wherein the penile prosthesis comprises a hydraulic penile prosthesis, and further comprising an implantable pump for operating the hydraulic penile prosthesis, the energy storage device supplying the energy for driving the pump.

172. An apparatus according to claim 171, wherein the pump is not a plunger type of pump.

173. An apparatus according to claim 139, wherein the energy transforming device generates as the energy of the second form a current exceeding 1 $\mu$A, when transferring the energy of the first form transmitted by the energy transmission device.

174. An apparatus according to claim 139, further comprising an adjustment device for adjusting the penile prosthesis to change between erect and flaccid penile states, wherein the adjustment device is adapted to mechanically adjust the penile prosthesis, or adapted to hydraulically adjust the penile prosthesis by using hydraulic means which is devoid of hydraulic fluid of the kind having a viscosity that substantially increases when exposed to heat or a magnetic field.

175. An apparatus according to claim 139, wherein the energy transforming device comprises at least one semiconductor type of component.

176. An apparatus according to claim 175, wherein the energy transforming device comprises a circuitry of semiconductor components.

177. An apparatus according to claim 175, wherein the semiconductor component comprises a transistor or microchip or similar electronic components excluding rectifying diodes.

178. An apparatus according to claim 176, wherein the semiconductor component comprises said element having a positive region and a negative region.

179. An apparatus according to claim 139, further comprising an implantable operation device for operating the penile prosthesis, wherein the energy storage device powers the operation device with the energy of the second form.

180. An apparatus according to claim 176, wherein the control device controls the operation device.

181. An apparatus according to claim 179, wherein the operation device comprises a motor.

182. An apparatus according to claim 181, further comprising an implantable gearing connected to the motor.

183. An apparatus according to claim 181, wherein the motor comprises a rotary motor and the control device controls the rotary motor to rotate a desired number of revolutions.

184. An apparatus according to claim 181, wherein the motor comprises a linear motor.

185. An apparatus according to claim 181, wherein the motor comprises a hydraulic or pneumatic fluid motor, and the control device controls the fluid motor.

186. An apparatus according to claim 181, wherein the motor comprises an electric motor having electrically conductive parts made of plastics.

187. An apparatus according to claim 179, wherein the penile prosthesis comprises hydraulic means and the operation device is adapted to conduct a hydraulic fluid in the hydraulic means.

188. An apparatus according to claim 187, wherein the operation device comprises a fluid conduit connected to the hydraulic means of the penile prosthesis, and a reservoir for fluid, the reservoir forming part of the conduit.

189. An apparatus according to claim 188, wherein the hydraulic means and conduit are devoid of any non-return valve.

190. An apparatus according to claim 189, wherein the reservoir forms a fluid chamber with a variable volume, and the operation device is adapted to distribute fluid from the chamber to the hydraulic means of the penile prosthesis by reduction of the volume of the chamber and to withdraw fluid from the hydraulic means to the chamber by expansion of the volume of the chamber.

191. An apparatus according to claim 190, wherein the operation device comprises an implantable motor used for reducing and expanding the volume of the chamber.

192. An apparatus according to claim 187, wherein the operation device comprises an implantable pump for pumping the hydraulic fluid in the hydraulic means of the penile prosthesis.

193. An apparatus according to claim 181, wherein the operation device comprises an electric motor and the energy of the second form comprises electric energy.

194. An apparatus according to claim 139, wherein the penile prosthesis is operable to perform a reversible function.

195. An apparatus according to claim 194, further comprising a reversing device implantable in the patient for reversing the function performed by the penile prosthesis.

196. An apparatus according to claim 195, wherein the control device controls the reversing device to reverse the function performed by the penile prosthesis.

197. An apparatus according to claim 195, wherein the reversing device comprises hydraulic means including a valve for shifting the flow direction of a fluid flow in the hydraulic means.

198. An apparatus according to claim 195, wherein the reversing device comprises a mechanical reversing device.

199. An apparatus according to claim 198, wherein the reversing device comprises a gearbox.

200. An apparatus according to claim 195, wherein the reversing device comprises a switch.

201. An apparatus according to claim 200, wherein the switch is operable by the energy of the second form.

202. An apparatus according to claim 201, wherein the control device controls the operation of the switch by shifting polarity of the energy of the second form.

203. An apparatus according to claim 201, wherein the switch comprises an electric switch and the energy of the second form comprises electric energy.

204. An apparatus according to claim 179, wherein the operation device comprises hydraulic means and at least one valve for controlling a fluid flow in the hydraulic means.

205. An apparatus according to claim 204, wherein the control device comprises a wireless remote control for controlling the valve.

206. An apparatus according to claim 139, further comprising an activatable source of energy implantable in the patient, wherein the source of energy is activated by wireless energy transmitted by the energy transmission device, to supply energy which is used in connection with the operation of the penile prosthesis.

207. An apparatus according to claim 139, wherein the energy transmission device transmits energy by at least one wireless signal.

208. An apparatus according to claim 207, wherein the signal contains radiant energy.

209. An apparatus according to claim 207, wherein the signal comprises a wave signal.

210. An apparatus according to claim 209, wherein the wave signal comprises an electromagnetic wave signal including one of an infrared light signal, a visible light signal, an ultra violet light signal, a laser signal, a micro wave signal, a radio wave signal, an x-ray radiation signal, and a gamma radiation signal.

211. An apparatus according to claim 209, wherein the wave signal comprises a sound or ultrasound wave signal.

212. An apparatus according to claim 207, wherein the signal comprises a digital or analog signal, or a combination of a digital and analog signal.

213. An apparatus according to claim 139, wherein the energy of the first form transmitted by the energy transmission device comprises an electric, an electromagnetic or a magnetic field, or a combination thereof.

214. An apparatus according to claim 213, wherein the electric, electromagnetic or magnetic field, or the combination thereof is transmitted in pulses or digital pulses, or a combination of pulses and digital pulses by the energy transmission device.

215. An apparatus according to claim 213, wherein the electric, electromagnetic or magnetic field, or the combination thereof is transmitted in waves or analog pulses or a combination thereof by the energy transmission device.

216. An apparatus according to claim 139, wherein the energy transforming device transforms the energy of the first form into a direct current or pulsating direct current, or a combination of a direct current and pulsating direct current.

217. An apparatus according to claim 139, further comprising an implantable pulse generator for generating electrical pulses from the energy of the second form produced by the energy field.

218. An apparatus according to claim 139, further comprising at least one implantable sensor for sensing at least one physical parameter of the patient, preferably ejaculation.

219. An apparatus according to claim 218, wherein the sensor comprises a pressure sensor for directly or indirectly sensing as the physical parameter the pressure in the urethra.

220. An apparatus according to claim 218, wherein the control device controls the penile prosthesis in response to signals from the sensor.

221. An apparatus according to claim 220, wherein the control device comprises an internal control unit implantable in the patient for controlling the penile prosthesis in response to signals from the sensor.

222. An apparatus according to claim 221, wherein the internal control unit directly controls the penile prosthesis in response to signals from the sensor.

223. An apparatus according to claim 220, wherein the control device comprises an external control unit outside the patient's body for controlling the penile prosthesis in response to signals from the sensor.

224. An apparatus according to claim 223, wherein the external control unit stores information on the physical parameter sensed by the sensor and is manually operated to control the penile prosthesis based on the stored information.

225. An apparatus according to claim 218, further comprising at least one implantable sender for sending information on the physical parameter sensed by the sensor.

226. An apparatus according to claim 139, wherein the control device comprises a wireless remote control for transmitting at least one wireless control signal for controlling the penile prosthesis.

227. An apparatus according to claim 226, wherein the control signal comprises a frequency, amplitude or frequency or amplitude modulated signal.

228. An apparatus according to claim 226, wherein the control signal comprises an analog or a digital signal, or a combination of an analog and digital signal.

229. An apparatus according to claim 226, wherein the remote control is adapted to obtain information on the condition of the implantable penile prosthesis and to control the penile prosthesis in response to the information.

230. An apparatus according to claim 226, wherein the control device comprises an implantable control unit for controlling the penile prosthesis.

231. An apparatus according to claim 230, wherein the control unit comprises a microprocessor.

232. An apparatus according to claim 226, wherein the wireless remote control comprises at least one external signal transmitter or transceiver and at least one internal signal receiver or transceiver implantable in the patient.

233. An apparatus according to claim 226, wherein the wireless remote control comprises at least one external signal receiver or transceiver and at least one internal signal transmitter or transceiver implantable in the patient.

234. An apparatus according to claim 226, wherein the remote control is adapted to send information related to the penile prosthesis from inside the patients body to the outside thereof.

235. An apparatus according to claim 234, wherein the remote control controls the penile prosthesis in response to the information.

236. An apparatus according to claim 226, wherein the remote control comprises a control signal transmitter for transmitting the wireless control signal, and the energy transmission device comprises the control signal transmitter, whereby energy is transmitted by the control signal.

237. An apparatus according to claim 226, wherein the energy transmission device transmits energy by at least one signal separate from the control signal.

238. An apparatus according to claim 226, wherein the remote control transmits a carrier signal for carrying the control signal.

239. An apparatus according to claim 226, wherein the energy transmission device transmits energy by at least one signal, which is used as a carrier signal for the control signal transmitted by the remote control.

240. An apparatus according to claim 239, wherein the carrier signal is frequency, amplitude or frequency and amplitude modulated.

241. An apparatus according to claim 239, wherein the carrier signal comprises digital, analog or a combination of digital and analog signals.

242. An apparatus according to claim 241, wherein the signals comprise wave signals.

243. An apparatus according to claim 226, wherein the control signal comprises a wave signal comprising one of a sound wave signal, an ultrasound wave signal, an electromagnetic wave signal, an infrared light signal, a visible light signal, an ultra violet light signal, a laser light signal, a micro wave signal, a radio wave signal, an x-ray radiation signal and a gamma radiation signal.

244. An apparatus according to claim 226, wherein the control signal comprises an electric or magnetic field, or a combined electric and magnetic field.

245. An apparatus according to claim 228, wherein the remote control transmits an electromagnetic carrier wave signal for carrying the digital or analog control signal.

246. An apparatus according to claim 139, wherein the energy of the second form used for operating the penile prosthesis is wirelessly transmitted by the energy transforming device.

247. An apparatus according to claim 139, wherein the control device comprises an implantable control unit for controlling the penile prosthesis.

248. An apparatus according to claim 247, wherein the control unit is programmable for controlling the penile prosthesis in accordance with a program.

249. An apparatus according to claim 247, wherein the control unit controls the penile prosthesis over time in accordance with an activity schedule program.

250. An apparatus according to claim 247, wherein the control device comprises an external wireless remote control for programming the implantable control unit.

251. An apparatus according to claim 139, further comprising an external data communicator and an implantable internal data communicator communicating with the external data communicator, wherein the internal communicator feeds data related to the penile prosthesis back to the external data communicator or the external data communicator feeds data to the internal data communicator.

252. An apparatus according to claim 251, wherein the internal data communicator feeds data related to at least one physical signal of the patient.

253. An apparatus according to claim 139, wherein the penile prosthesis is adapted to control the erect and flaccid states of the patient's penis.

254. An apparatus according to claim 139, wherein the penile prosthesis is non-inflatable.

255. An apparatus according to claim 139, wherein one of the energy of the first form and the energy of the second form comprises magnetic energy, kinetic energy, sound energy, chemical energy, radiant energy, electromagnetic energy, photo energy, nuclear energy or thermal energy.

256. An apparatus according to claim 139, wherein one of the energy of the first form and the energy of the second form is non-magnetic, non-kinetic, non-chemical, non-sonic, non-nuclear or non-thermal.

257. An apparatus according to claim 139, wherein the energy transmission device functions different from the energy transforming device.

258. An apparatus according to claim 139, wherein the energy transmission device functions similar to the energy transforming device.

259. An apparatus according to claim 139, wherein the penile prosthesis is embedded in a soft or gel-like material.

260. An apparatus according to claim 139, wherein the penile prosthesis is embedded in a silicone material having hardness less than 20 Shore.

261. A male sexual impotence treatment prosthesis apparatus, comprising:
an operable prosthesis implantable in the cavities of the corpora cavernosa of an impotent patient to provide erect penile condition, when the prosthesis is operated,
a source of energy implantable in the patient for supplying energy for the operation of the penile prosthesis, and
an energy transmission device adapted to wirelessly transmit energy from outside the patient's body to inside the patient's body to directly or indirectly control the supply of energy from the source of energy.

262. An apparatus according to claim 261, further comprising a switch implantable in the patient for directly or indirectly switching the supply of energy from the source of energy.

263. An apparatus according to claim 262, wherein the switch is directly operated by the energy wirelessly transmitted by the energy transmission device to switch from an off mode, in which the source of energy is not in use, to an on mode, in which the source of energy supplies energy for the operation of the penile prosthesis.

264. An apparatus according to claim 262, further comprising a remote control for controlling the supply of energy from the implantable source of energy, wherein the switch is operated by the energy wirelessly transmitted by the energy transmission device to switch from an off mode, in which the remote control is prevented from controlling the source of energy and the source of energy is not in use, to a standby mode, in which the remote control is permitted to control the source of energy to supply energy for the operation of the penile prosthesis.

265. An apparatus according to claim 261, wherein the energy transmission device wirelessly transmits energy of a first form, further comprising an energy transforming device implantable in the patient for transforming the energy of the first form into energy of a second form, the penile prosthesis being operable in response to the energy of the second form.

266. An apparatus according to claim 265, further comprising a switch implantable in the patient for directly or indirectly switching the supply of energy from the source of energy.

267. An apparatus according to claim 266, wherein the switch is operated by the energy of the second form supplied by the energy transforming device to switch from an off mode, in which the source of energy is not in use, to an on mode, in which the source of energy supplies energy for the operation of the penile prosthesis.

268. An apparatus according to claim 267, further comprising a remote control for controlling the supply of energy of the implantable source of energy, wherein the switch is operated by the energy of the second form supplied by the energy transforming device to switch from an off mode, in which the remote control is prevented from controlling the source of energy and the source of energy is not in use, to a standby mode, in which the remote control is permitted to control the source of energy to supply energy for the operation of the penile prosthesis.

269. A male sexual impotence treatment prosthesis apparatus, comprising:
an operable prosthesis implantable in the cavities of the corpora cavernosa of an impotent patient to provide erect penile condition, when the prosthesis is operated,
an energy transmission device for wireless transmission of energy of a first form from outside the patient's body to inside the patient's body for use in connection with the operation of the prosthesis, when the prosthesis is implanted, and
an energy transforming device implantable in the patient for transforming the energy of the first form wirelessly transmitted by the energy transmission device into energy of a second form, the penile prosthesis being operable in response to the energy of the second form,
wherein the energy transforming device includes at least one semiconductor type of component or a circuitry of semiconductor components.

270. An apparatus according to claim 269, wherein the semiconductor component comprises a transistor or microchip or similar electronic components excluding rectifying diodes.

271. A male sexual impotence treatment prosthesis apparatus, comprising:
an operable prosthesis implantable in the cavities of the corpora cavernosa of an impotent patient to provide erect penile condition, when the prosthesis is operated,
an implantable operation device for operating the penile prosthesis, and
an energy transmission device for wireless transmission of energy of a first form from outside the patient's body to inside the patient's body for direct power of the operation device,
wherein the operation device transforms the energy of the first form into energy of a second form, the energy of the second form being kinetic energy.

272. An apparatus according to claim 271, wherein the energy transmission device is adapted to transmit wireless energy in the form of an electric, an electromagnetic or a magnetic field, or a combination thereof for direct power of the operation device.

273. An apparatus according to claim 271, wherein the operation device comprises a motor for direct or intermittent operation of the penile prosthesis.

274. An apparatus according to claim 273, wherein the penile prosthesis is operable to perform a reversible function and the motor is adapted to reverse said function.

275. An apparatus according to claim 271, wherein the penile prosthesis comprises a hydraulic penile prosthesis, and the operation device comprises an implantable pump for operating the hydraulic penile prosthesis.

276. An apparatus according to claim 175, wherein the pump is not a plunger type of pump.

277. An apparatus according to claim 271, further comprising an adjustment device for adjusting the penile prosthesis to change between erect and flaccid penile states, wherein the adjustment device is adapted to mechanically adjust the penile prosthesis, or adapted to hydraulically adjust the penile prosthesis by using hydraulic means which is devoid of hydraulic fluid of the kind having a viscosity that substantially increases when exposed to heat or a magnetic field.

278. An apparatus according to claim 271, further comprising a control device for controlling the operation device.

279. An apparatus according to claim 278, wherein the operation device comprises a motor.

280. An apparatus according to claim 279, further comprising an implantable gearing connected to the motor.

281. An apparatus according to claim 279, wherein the motor comprises a rotary motor and the control device controls the rotary motor to rotate a desired number of revolutions.

282. An apparatus according to claim 279, wherein the motor comprises a linear motor.

283. An apparatus according to claim 279, wherein the motor comprises a hydraulic or pneumatic fluid motor, and the control device controls the fluid motor.

284. An apparatus according to claim 279, wherein the energy of the first form comprises electric energy and the motor comprises an electric motor.

285. An apparatus according to claim 271, wherein the penile prosthesis comprises hydraulic means and the operation device is adapted to conduct a hydraulic fluid in the hydraulic means.

286. An apparatus according to claim 285, wherein the operation device comprises a fluid conduit connected to the hydraulic means of the penile prosthesis, and a reservoir for fluid, the reservoir forming part of the conduit.

287. An apparatus according to claim 286, wherein the hydraulic means and conduit are devoid of any non-return valve.

288. An apparatus according to claim 287, wherein the reservoir forms a fluid chamber with a variable volume, and the operation device is adapted to distribute fluid from the chamber to the hydraulic means of the penile prosthesis by reduction of the volume of the chamber and to withdraw fluid from the hydraulic means to the chamber by expansion of the volume of the chamber.

289. An apparatus according to claim 288, wherein the operation device comprises an implantable motor used for reducing and expanding the volume of the chamber.

290. An apparatus according to claim 285, wherein the operation device comprises an implantable pump for pumping the hydraulic fluid in the hydraulic means of the penile prosthesis.

291. An apparatus according to claim 271, wherein the penile prosthesis is operable to perform a reversible function.

292. An apparatus according to claim 291, further comprising a reversing device implantable in the patient for reversing the function performed by the penile prosthesis.

293. An apparatus according to claim 292, further comprising a control device, wherein the control device controls the reversing device to reverse the function performed by the penile prosthesis.

294. An apparatus according to claim 292, wherein the reversing device comprises hydraulic means including a valve for shifting the flow direction of a fluid flow in the hydraulic means.

295. An apparatus according to claim 292, wherein the reversing device comprises a mechanical reversing device.

296. An apparatus according to claim 292, wherein the reversing device comprises a gearbox.

297. An apparatus according to claim 292, wherein the reversing device comprises a switch.

298. An apparatus according to claim 271, wherein the operation device comprises hydraulic means and at least one valve for controlling a fluid flow in the hydraulic means.

299. An apparatus according to claim 298, further comprising a wireless remote control for controlling the valve.

300. An apparatus according to claim 271, further comprising a switch implantable in the patient for directly or indirectly switching the operation of the penile prosthesis.

301. An apparatus according to claim 271, wherein the energy transmission device transmits sound or ultrasound waves containing the wireless energy.

302. An apparatus according to claim 272, wherein the electric, electromagnetic or magnetic field, or the combination thereof is transmitted in pulses or digital pulses, or a combination of pulses and digital pulses by the energy transmission device.

303. An apparatus according to claim 272, wherein the electric, electromagnetic or magnetic field, or the combination thereof is transmitted in waves or analog pulses or a combination thereof by the energy transmission device.

304. An apparatus according to claim 271, further comprising at least one implantable sensor for sensing at least one physical parameter of the patient, preferably ejaculation.

305. An apparatus according to claim 304, wherein the sensor comprises a pressure sensor for directly or indirectly sensing as the physical parameter the pressure in the urethra.

306. An apparatus according to claim 304, further comprising a control device for controlling the penile prosthesis in response to signals from the sensor.

307. An apparatus according to claim 306, wherein the control device comprises an internal control unit implantable in the patient for controlling the penile prosthesis in response to signals from the sensor.

308. An apparatus according to claim 307, wherein the internal control unit directly controls the penile prosthesis in response to signals from the sensor.

309. An apparatus according to claim 306, wherein the control device comprises an external control unit outside the patient's body for controlling the penile prosthesis in response to signals from the sensor.

310. An apparatus according to claim 309, wherein the external control unit stores information on the physical parameter sensed by the sensor and is manually operated to control the penile prosthesis based on the stored information.

311. An apparatus according to claim 304, further comprising at least one implantable sender for sending information on the physical parameter sensed by the sensor.

312. An apparatus according to claim 271, further comprising a wireless remote control for transmitting at least one wireless control signal for controlling the penile prosthesis.

313. An apparatus according to claim 312, wherein the control signal comprises a frequency, amplitude or frequency or amplitude modulated signal.

314. An apparatus according to claim 312, wherein the control signal comprises an analog or a digital signal, or a combination of an analog and digital signal.

315. An apparatus according to claim 312, wherein the remote control is adapted to obtain information on the condition of the implantable penile prosthesis and to control the penile prosthesis in response to the information.

316. An apparatus according to claim 312, wherein the remote control comprises an implantable control unit for controlling the penile prosthesis.

317. An apparatus according to claim 316, wherein the control unit comprises a microprocessor.

318. An apparatus according to claim 312, wherein the wireless remote control comprises at least one external signal transmitter or transceiver and at least one internal signal receiver or transceiver implantable in the patient.

319. An apparatus according to claim 312, wherein the wireless remote control comprises at least one external signal receiver or transceiver and at least one internal signal transmitter or transceiver implantable in the patient.

320. An apparatus according to claim 312, wherein the remote control is adapted to send information related to the penile prosthesis from inside the patients body to the outside thereof.

321. An apparatus according to claim 320, wherein the remote control controls the penile prosthesis in response to the information.

322. An apparatus according to claim 312, wherein the remote control transmits a carrier signal for carrying the control signal.

323. An apparatus according to claim 312, wherein the control signal comprises a wave signal comprising one of a sound wave signal, an ultrasound wave signal, an electromagnetic wave signal, an infrared light signal, a visible light signal, an ultra violet light signal, a laser light signal, a micro wave signal, a radio wave signal, an x-ray radiation signal and a gamma radiation signal.

324. An apparatus according to claim 312, wherein the control signal comprises an electric or magnetic field, or a combined electric and magnetic field.

325. An apparatus according to claim 314, wherein the remote control transmits an electromagnetic carrier wave signal for carrying the digital or analog control signal.

326. An apparatus according to claim 271, further comprising an implantable control unit for controlling the penile prosthesis.

327. An apparatus according to claim 326, wherein the control unit is programmable for controlling the penile prosthesis in accordance with a program.

328. An apparatus according to claim 326, wherein the control unit controls the penile prosthesis over time in accordance with an activity schedule program 329. An apparatus according to claim 326, further comprising an external wireless remote control for programming the implantable control unit.

330. An apparatus according to claim 271, further comprising an external data communicator and an implantable internal data communicator communicating with the external data communicator, wherein the internal communicator feeds data related to the penile prosthesis back to the external data communicator or the external data communicator feeds data to the internal data communicator.

331. An apparatus according to claim 330, wherein the internal data communicator feeds data related to at least one physical signal of the patient.

332. An apparatus according to claim 271, wherein the penile prosthesis is adapted to control the erect and flaccid states of the patient's penis.

333. An apparatus according to claim 271, wherein the penile prosthesis is non-inflatable.

334. An apparatus according to claim 271, wherein the penile prosthesis is embedded in a soft or gel-like material.

335. An apparatus according to claim 271, wherein the penile prosthesis is embedded in a silicone material having hardness less than 20 Shore.

* * * * *